United States Patent
Allison et al.

(10) Patent No.: US 6,609,014 B1
(45) Date of Patent: Aug. 19, 2003

(54) USE OF PDT TO INHIBIT INTIMAL HYPERPLASIA

(75) Inventors: Beth Anne Allison, Vancouver (CA); Philippe Maria Clotaire Margaron, Burnaby (CA); York N. Hsiang, Vancouver (CA)

(73) Assignees: QLT Inc. (CA); The University of British Columbia (CA)

(*) Notice: Subject to any disclaimer, the term of this patent is extended or adjusted under 35 U.S.C. 154(b) by 16 days.

(21) Appl. No.: 09/716,022

(22) Filed: Nov. 17, 2000

Related U.S. Application Data

(60) Provisional application No. 60/165,939, filed on Nov. 17, 1999, and provisional application No. 60/129,324, filed on Apr. 14, 1999.

(51) Int. Cl.$^7$ .......................... A61B 5/00; A61B 18/18; A61N 1/30

(52) U.S. Cl. ................. 600/310; 600/342; 604/21; 606/15

(58) Field of Search .................. 600/310, 342; 604/21; 606/15, 2; 128/898; 514/410

(56) References Cited

U.S. PATENT DOCUMENTS

| | | | |
|---|---|---|---|
| 5,015,584 A | 5/1991 | Brysk .................... | 435/240.23 |
| 5,171,749 A | 12/1992 | Levy et al. ................. | 514/410 |
| 5,192,312 A | 3/1993 | Orton ............................ | 623/2 |
| 5,200,400 A | 4/1993 | Teramoto et al. ............. | 514/45 |
| 5,298,018 A * | 3/1994 | Narciso, Jr. ................. | 128/898 |
| 5,422,362 A * | 6/1995 | Vincent et al. ............. | 514/410 |
| 5,834,503 A * | 11/1998 | Kelly et al. ................. | 514/410 |
| 5,880,145 A | 3/1999 | Sternberg et al. ........... | 514/410 |
| 5,929,105 A | 7/1999 | Sternberg et al. ........... | 514/410 |
| 6,235,767 B1 * | 5/2001 | Kelly et al. ................. | 514/410 |
| 6,366,719 B1 * | 4/2002 | Heath et al. ................ | 385/147 |

FOREIGN PATENT DOCUMENTS

| | | |
|---|---|---|
| EP | 906758 | 4/1999 |
| WO | WO 0021562 | 4/2000 |
| WO | WO 0124825 | 4/2001 |

OTHER PUBLICATIONS

Adili, F. et al. (1998). "Photodynamic therapy with local photosensitizer delivery inhibits experimental intimal hyperplasia" *Lasers In Surgery and Medicine* 23(5):263–73.

Adili, F, et al. (1999). "Significance of dosimetry in photodynamic therapy of injured arteries: classification of biological responses" *Photochemistry and Photobiology* 70(4):663–8.

Burbridge, G.E., et al. (1976). "Late complications and results of bovine xenografts" *Trans Am Soc Artif Intern Organs*, 22, 377–81.

Byrne, C., et al. (1994). "Effect of age and diagnosis on survival of older patients beginning chronic dialysis." *Jama*, 271, 34–6.

Dartsch, P.C., et al. (1990). "Responses of cultured smooth muscle cells from human nonatherosclerotic arteries and primary stenosing lesions after photoradiation: implications for photodynamic therapy of vascular stenoses" *J Am Coll Cardiol*, 15, 1545–50.

Dilley, R.J., et al. (1988). "A review of the histologic changes in vein–to–artery grafts, with particular reference to intimal hyperplasia" *Arch Surg*, 123, 691–6.

(List continued on next page.)

*Primary Examiner*—William C. Doerrler
(74) *Attorney, Agent, or Firm*—Morrison & Foerster LLP

(57) ABSTRACT

Long-term dialysis requires provision of safe and reliable vascular access, often in the form of an arteriovenous (AV) fistula. The primary cause of AV fistula loss or failure is stenosis caused by intimal hyperplasia (IH) in the graft at the venous anastomosis or the distal vein. Disclosed are methods of using photodynamic therapy (PDT) to inhibit IH in blood vessels which may also be used to inhibit IH and SMC growth at the anastomosis of an AV fistula in vivo.

22 Claims, 11 Drawing Sheets

OTHER PUBLICATIONS

Diskin CJ, S.T., et al. (1993). "Pharmacological intervention to prevent intimal hyperplasia" *In Vascular Access For Hemodialysis, vol. III*. WL Gore and Associates, Inc. and Precept Press, Inc., pp. 41–73.

Dougherty, T.J. (1987). "Photosensitizers: therapy and detection of malignant tumors" *Photochem Photobiol*, 45, 879–89.

Excerpts from the United States Renal Data System Annual Report. (1998) *American J. Kidney Dis.*, 32, S9–S141.

Hsiang, Y.N., et al. (1995). "Dosage and timing of photofrin for photodynamic therapy of intimal hyperplasia" *Cardiovascular Suurgery* 3(5):489–94.

Humphries AL, et al. (1989). "Alternative plans for vascular access for hemodialysis" *In . Vascular Access for Hemodialysis vol. I*. WL Gore and Associates, Inc. and Pluribus Press, Inc.

Hunt, D.W., et al. (1999). "Consequences of the photodynamic treatment of resting and activated peripheral T lymphocytes" *Immunopharmacology*, 41, 31–44.

Hurt, A.V., et al. (1983) "Bovine carotid artery heterografts versus polytetrafluoroethylene grafts. A prospective, randomized study." *Am J Surg*, 146, 844–7.

Kaplan MP, et al. (1989). "An analysis of early (two week) failure of vascular access" *In Vascular Access for Hemodialysis, vol. III*. WL Gore and Associates, Inc. and Pluribus Press, Inc., pp. 114–123.

LaMuraglia, G.M., et al. (1994). "Photodynamic therapy inhibition of experimental intimal hyperplasia: acute and chronic effects" *J Vasc Surg*, 19, 321–9; discussion 329–31.

LaMuraglia, G.M., et al. (1995). "Photodynamic therapy of vein grafts: suppression of intimal hyperplasia of the vein graft but not the anastomosis" *J Vasc Surg*, 21, 882–90; discussion 889–90.

Leapman, S.B., et al. (1996) "The arteriovenous fistula for hemodialysis access: gold standard or archaic relic?" *Am Surg*, 62, 652–6; discussion 656–7.

Leapman SB, et al. (1993). "Salvage surgery for arteriovenous conduits: does it make sense?" *In Vascular Access for Hemodialysis –III*. WL Gore and Associates, Inc. and Precept Press.

Luke, R.G. (1998). "Chronic renal failure–a vasculopathic state." *N Engl J Med*, 339, 841–3.

Mansfield, R. et al. (2000). Optimisation of sensitiser dose in endovascular photodynamic therapy *Clinical Science* 99(2):P3.

Obochi, Modestus, et al. (1997). "Immunomodulatory properties of PDT: prolonged skin graft survival following low–dose PDT of doner tissues" *Photochemistry and Photobiology* 65:18S–19S.

Obochi, Modestus, et al. (1997). "Prevention of skin allograft rejection by photodynamic therapy (PDT) using venzoporphyrin–derivative monoacid ring a (BPD) verteporfin" *Dissertation Abstracts International* 58(6):1–2.

Obochi, Modestus, et al. (1997). "Prolonged skin allograft survival after photodynamic therapy associated with modification of donor skin antigenicity" *Transplantation* 63(6):810–817.

Ortu, P., et al. (1992). "Photodynamic therapy of arteries. A novel approach for treatment of experimental intimal hyperplasia" *Circulation*, 85, 1189–96.

Pond, W. "Nutrition and the cardiovascular system of swine" *In Swine in Cardiovascular Research, vol. II*. CRC Press: Boca Raton Florida.

Redmond, et al. (1999). "A compilation of singlet oxygen yields from biologically relevant molecules" *Photochemistry and Photobiology*, 70(4):391–475.

Sindermann, J.R. & March, K.L. (1998). "Heparin responsiveness in vitro as a prognostic tool for vascular graft stenosis: a tale of two cell types?" *Circulation*, 97, 2486–90.

Sobeh, M.S., et al. (1995). "Photodynamic therapy in a cell culture model of human intimal hyperplasia" *Eur J Vasc Endovasc Surg*, 9, 463–8.

Statius van Eps, R.G., et al. (1997). "Photodynamic therapy of extracellular matrix stimulates endothelial cell growth by inactivation of matrix–associated transforming growth factor–beta" *Lab Invest*, 76, 257–66.

Tellis, V.A., et al. (1979). "Expanded polytetrafluoroethylene graft fistula for chronic hemodialysis" *Ann Surg*, 189, 101–5.

Tellis, V., et al. (1969). "Internal arteriovenous fistulae in a hemodialysis–transplant program" *Trans Am Soc Artif Intern Organs*, 15, 293–7.

Westerband, A., et al. (1998). "Topography of cell replication in human vein graft stenoses" *Circulation*, 98, II325–9; discussion II329–30.

\* cited by examiner

*p<0.05

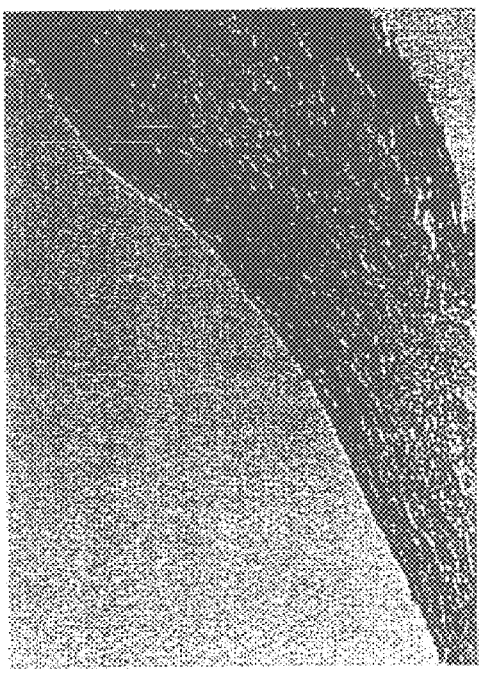 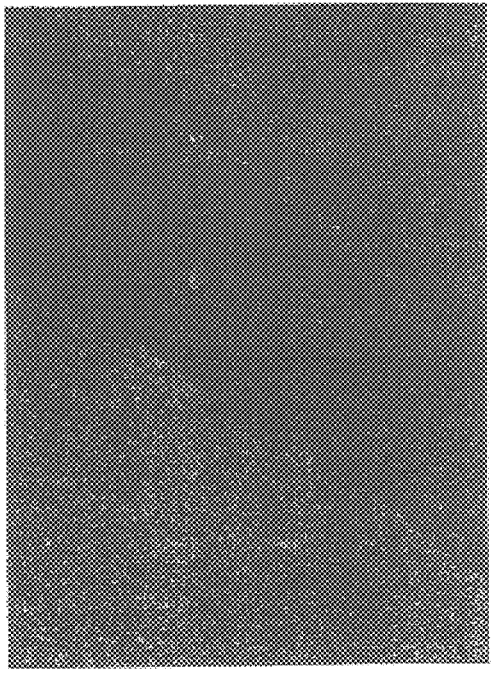
FIG. 11A                    FIG. 11B

USE OF PDT TO INHIBIT INTIMAL HYPERPLASIA

RELATED APPLICATIONS

The present application claims benefit of priority from Ser. No. 60/165,939, filed Nov. 17, 1999, which is hereby incorporated by reference in its entirety as if fully set forth. The present application is also related to U.S. patent application Ser. No. 09/169,233, filed Oct. 9, 1998, and Ser. No. 60/129,324, filed Apr. 14, 1999, both of which are hereby incorporated by reference in their entirety, as if fully set forth.

TECHNICAL FIELD

The invention relates to the use of low-dose photodynamic therapy (PDT) to inhibit or reduce stenosis caused by intimal hyperplasia (IH) in blood vessels. In particular, the treatment of IH at an anastomosis of a graft or conduit providing vascular access, such as an arteriovenous (AV) fistula, is disclosed. The invention also relates to inhibiting or reducing the smooth muscle cell (SMC) growth component of IH by low-dose PDT.

BACKGROUND ART

Patients with chronic renal failure in the United States number approximately 2 million, with 220,000 receiving dialysis therapy as of 1998 (1). The current annual increase in the number of patients receiving chronic hemodialysis is 6 to 7 percent due to acceptance of older candidates, patients living longer, the scarcity of transplantable kidneys, and the loss of transplanted kidneys, returning people to dialysis (1,2). Long-term dialysis requires provision of safe and reliable vascular access, often in the form of an arteriovenous (AV) fistula or an AV conduit, usually made of polytetrafluoroethylene (PTFE)(3,4,5). Unfortunately the failure rate of access fistulae can be as high as 60% at one year, with the mean time from insertion to first repair being only 10 months (6,7).

The primary cause of AV fistula or AV conduit loss or failure is stenosis caused by intimal hyperplasia (IH), which includes a smooth muscle cell (SMC) growth component, in the graft at the venous anastomosis or the distal vein (8). IH leads to formation of a thickened fibromuscular layer between the vein endothelium and the inner elastic lamina (IEL). Excessive thickening of the intima can lead to luminal narrowing and reduction of blood flow to such an extent that thrombosis occurs (9). This early failure represents the destruction of a useful access site, ultimately compromising the life of a patient dependent on dialysis (10). Mortality among dialysis patients, although slowly declining, remains at 20 percent per year (11).

Considerable research has aimed at pharmacological intervention to prevent intimal hyperplasia, and although a number of agents have shown great promise in animal or angioplasty models—very few have been shown to be of any benefit in hemodialysis patients (12). Photodynamic therapy (PDT) is an approach that has been investigated for the inhibition of intimal hyperplasia in other settings (see U.S. Pat. No. 5,422,362, which is hereby incorporated by reference). PDT generally involves administration of an inert photosensitizer (PS) that becomes activated by a specific wavelength of light. Once activated, PS produces toxic oxygen species that cause cell death by affecting cell membranes and subcellular organelles (13) or, when used in low doses, modulate cell behavior (14,15,16).

Intimal hyperplasia has been successfully inhibited in animal models involving balloon-catheter induced injury to arteries by PDT (17,18), and human SMCs isolated from arteries and veins have been shown to be susceptible to PDT (19,20). LaMuraglia et al. have investigated the efficacy of PDT to reduce vein graft IH. Although their "ex vivo" PDT protocol led to suppression of IH in the body of the vein graft, it did not affect IH at the anastomosis of the vein graft to an artery (21).

DISCLOSURE OF THE INVENTION

The present invention relates to methods of using photodynamic therapy (PDT) to prevent, treat, inhibit or reduce intimal hyperplasia (IH) in blood vessels in vivo. In particular the methods may be applied to the in vivo prevention and/or treatment of stenosis in an anastomosis, such as at those of an arteriovenous (AV) fistula or conduit. The methods of the invention may be used in any vein, artery, and/or vascular graft, and include the combined use of a photosensitizer (PS) and radiation sources for irradiation that offer advantages over previous methods of treating blood vessels and anastomoses, including those of AV fistulae or conduits. The PS may be delivered systemically, locally, and even directly into the lumen of the blood vessel tissue to be treated. Local delivery of the PS provides a high local concentration while reducing the likelihood of transient skin photosensitivity that might follow systemic PS administration.

Following, or simultaneous with, PS administration, treatment with radiation absorbed by the PS may be performed by any means, including direct irradiation of the anastomosis, the blood vessel tissue containing it, or a larger area containing the anastomosis and other tissues, or extraluminal irradiation from the adventitia using ambient light or a flexible patch diffuser. In a preferred embodiment, the radiation is applied via a flexible patch diffuser that can be wrapped around the blood vessel. This permits the use of lower light intensities that inhibit IH inhibit (IH) without compromising the blood vessel's wall.

BRIEF DESCRIPTION OF THE DRAWINGS

FIGS. 11A and 11B show immunohistochemical staining for monocytes/macrophages. Shown are representative portions of cross-sections of veins from PDT treated (11A) and control (11B) fistulae 48 hours after fistula creation after staining with an anti-human monocyte/macrophage monoclonal antibody (arrows, 16× magnification).

FIGS. 12A and 12B show cross-sections of veins from PDT treated (12A) and control (12B) fistulae 48 hours after creation. The darker line (arrows) surrounding the lumen of each vein is indicative of a single layer of endothelial cells stained with anti-von Willebrand factor antibody (5× magnification). FIG. 12C is a 16× magnification of a portion of the PDT treated vein showing an uninterrupted endothelial cell layer (dark brown staining on lumen side, see arrows).

MODE OF CARRYING OUT THE INVENTION

Figure 1A:
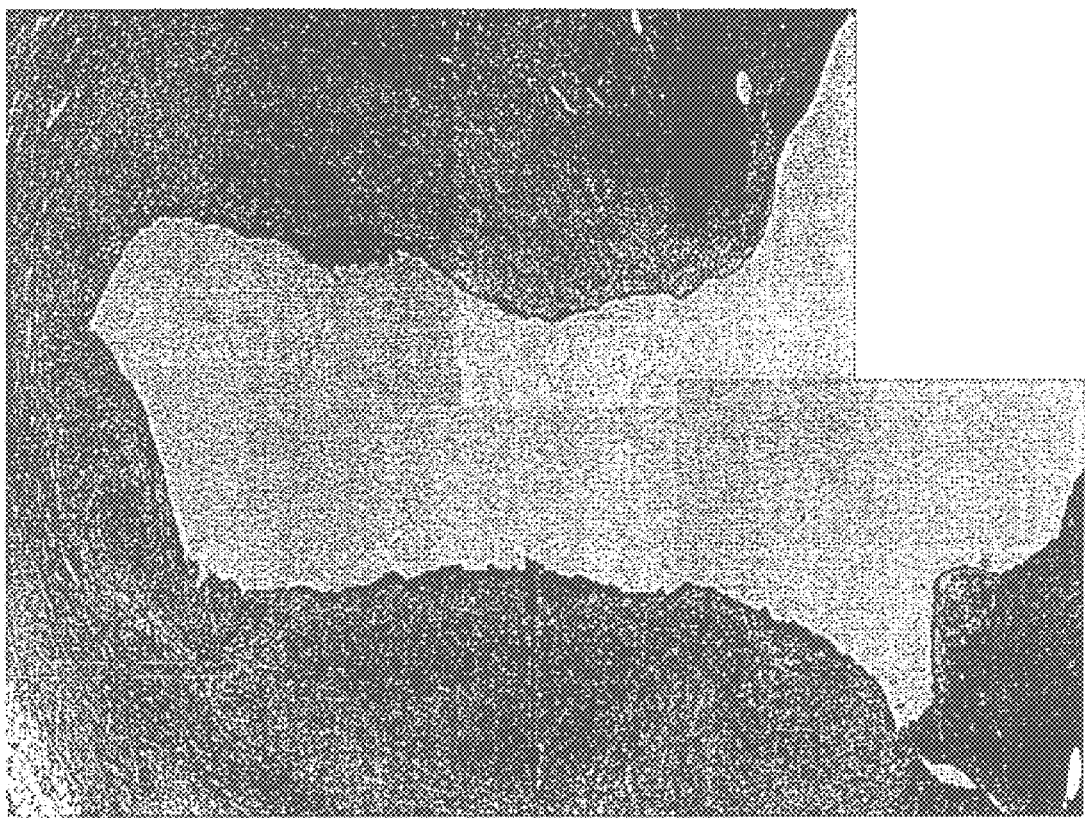
FIG. 1A is a photomicrograph of an AV fistula in cross-section. Considerable intimal hyperplasia is visible on the venous side of the anastomosis (arrow) between the Internal Elasic Lamina (darker stained line) and the endothelial cell lining at the lumen (Elastin stai X25).

The methods of the invention are directed to the use of a photosensitizer (PS) in photodynamic therapy (PDT) to prevent, treat, inhibit or reduce intimal hyperplasia (IH) in blood vessels in vivo. In particular, the methods prevent and/or act on stenosis occurring at anastomoses in blood vessels. As used herein, "anastomosis" refers to any bridge or connection, including joint or suture, between two surfaces. Anastomoses include both natural, such as an anastomotic network of arteries, and iatrogenic, such as by surgical connection, bridges or connections. Stated differently, anastomosis generally refers to any connection of hollow organs, such as blood vessels, ureters, bronchi, and bowels. One example of such a connection is an arteriovenous (AV) fistula in kidney dialysis patients.

An AV fistula is a connection between an artery and a vein. The junction between the artery and the vein is known as anastomosis. While the vein may be termed "arterialized", it should, however, still be considered a vein. A graft is a natural or prosthetic conduit, such as a vein graft, connecting two blood vessels. A nonlimiting example of prosthetic material is polytetrafluoroethylene (PTFE).

Also as used herein, IH is defined as a pathophysiological phenomenon which results in the occlusion of the vasculature and is accompanied by the proliferation of cells including smooth muscle cells (SMCs) in the intima tunica. No part, or combination of parts, of this definition implies that the methods of the invention necessarily directly inhibits SMC proliferation. The conditions which the methods of the invention are designed to treat, however, often include such proliferation. IH may result in stenosis within the body of a blood vessel.

In particular the methods of the invention are applied to the in vivo prevention, inhibition, and/or treatment of IH or stenosis in arteriovenous (AV) fistula. Additionally, the methods may be applied to prevent and/or treat IH or stenosis in veins at the venous anastomosis of an arteriovenous graft for hemodialysis; in a vein graft such as those at an artery-vein or artery-artery graft; in a blood vessel distal from the venous anastomosis; in a coronary artery bypass graft using a saphenous vein or mammary arteries; and within a large central vein. More particularly, the methods are directed to the treatment of AV fistulae in human patients undergoing kidney dialysis. An additional indication where the present methods may be useful is central venous catheterization.

The methods include the administration of a photosensitizer (PS) and irradiation with a wavelength of electromagnetic radiation capable of activating the PS.

Preferred PSs of the invention are the green porphyrins, and preferred irradiation is with visible light. A particularly preferred PS is a lipid formulation of benzoporphyrin derivative monoacid ring A, which is also known as verteporfin or BPD-MA. Following, or simultaneous with, delivery of the PS, irradiation may be performed by any radiation source. Examples of sources of visible light radiation include operating room lamps, halogen lamps, fluorescent lamps, laser light sources, and combinations thereof. Additional examples of light sources include light emitting diode (LED) panels or flexible light diffusers which may be wrapped around a blood vessel.

Preferably, radiation, such as 690 nm light in the case of BPD-MA use, is delivered to the blood vessel. In one embodiment, the exterior (adventitia) of a BPD-MA treated blood vessel is exposed to 40 minutes of an operating room (OR) lamp light, which may be substituted by any other similar radiation source. This extraluminal mode of light delivery offer significant advantages over previous methods of treating blood vessels such as vein grafts by allowing the use of lower light intensities that inhibit IH without compromising the relatively thin venous wall.

Also preferred in the invention is the use of low-dose PDT. High dose PDT will result in massive destruction of blood vessel tissue. By "low-dose PDT", it is meant a total photodynamic therapy experience at substantially lower levels of intensity than that ordinarily employed. Generally, there are three significant variables—the concentration of the photosensitizing drug, the intensity of the radiation employed and the time of exposure to light, which determines the total amount of energy ultimately delivered to the target tissue. Generally, an increase in one of these factors permits a decrease in the others.

For example, if it is desired to irradiate only for a short period of time the energy of irradiation or the concentration of the drug may be increased. Conversely, if longer time periods of irradiation are permitted, lower irradiation intensities and lower drug concentrations are desirable. As exemplified below, the combination of 0.15 mg BPD-MA as a drug concentration and approximately 1 $J/cm^2$ total radiation from an appropriate radiation source provided successful results. The use of low dose PDT offers an additional advantage in the form of reducing the likelihood of PDT side effects such as damage to the venous wall or surrounding tissue. Low dose PDT permits treatment that minimizes obvious cell death which would result in inflammation and probably further IH if not immediate thrombotic occlusion of the blood vessel.

It is understood that the manipulation of these parameters will vary according to the nature of the blood vessel tissue being treated and the nature of the PS employed. However, in general, low-dose PDT employs combinations of the drug concentration, intensity, and total energy values which are several fold lower than those conventionally used for destroying target tissues such as tumors and unwanted neovascularization. One measure might be the product of PS concentration (e.g., in ng/ml)×intensity (e.g., in 2) mW/cm$^2$)×time (e.g., in seconds). However, it is difficult to set absolute numbers for this product since there are constraints on each of the parameters individually. For example, if the intensity is too low, the PS will not be activated consistently; if the intensity is too high, hyperthermic and other damaging effects may occur. Similarly, PS concentrations cannot vary over any arbitrary range. There may also be constraints on the time during which radiation can be administered. Accordingly, the product of the foregoing equation is only a rough measure. However, this approach may provide a convenient index that can be adjusted according to the relative potency of the PS employed, and in general, an increase in intensity would permit a decrease in time of irradiation, and so forth.

An additional aspect of the invention includes PDT mediated decreases in the number of actively dividing cells in the media of the treated blood vessels within 48 hours after fistula creation, without necessarily having a direct cytotoxic effect on SMC.

The probable largest practical application of this invention is on IH in a vein grafts of an AV fistula or conduit, such as those used for human patients undergoing kidney dialysis. In particular, application to the venous end of an arteriovenous graft, as well as other sites in the distal effluent vein, including the central veins, and the body of a vein graft connecting an artery to vein or artery to artery, is contemplated. However, any vein graft may also be treated by the methods of the invention. The particular structure or composition of the vein graft is not a limiting factor to the applicability of the invention's methods. Thus veterinary uses of the technique of the invention are contemplated, as well as uses in animal research models.

According to the methods of the invention, the target vein graft or anastomosis is first treated with a PS. Administration of the PS may be by delivery using any appropriate means including, but not limited to, systemic, local, or even direct application into the lumen of the target vein tissue. Local delivery of the PS provides a high local concentration while reducing the likelihood of transient skin photosensitivity or other undesirable side effects that may follow systemic PS administration. Suitable PSs are of a wide variety, including, without limitation, porphyrin related compounds such as hematoporphyrin derivative, Photofrin® porfimer sodium, the green porphyrins such as the BPDs, purpurins, chlorins, fluorins, etiopurpurins, and the like as well as phthalocyanines, pheophorbides, deuteroporphyrins, texaphrins, and the like.

Examples of these and other PSs for use in the present invention include, but are not limited to, angelicins, some biological macromolecules such as lipofuscin; photosystem II reaction centers; and D1-D2-cyt b-559 photosystem H reaction centers, chalcogenapyrillium dyes, chlorins, chlorophylls, coumarins, cyanines, ceratin DNA and related compounds such as adenosine; cytosine; 2'-deoxyguanosine-5'-monophosphate; deoxyribonucleic acid; guanine; 4-thiouridine; 2'-thymidine 5'-monophosphate; thymidylyl(3'-5')-2'-deoxyadenosine; thymidylyl(3'-5')-2'-deoxyguanosine; thymine; and uracil, certain drugs such as adriamycin; afloqualone; amodiaquine dihydrochloride; chloroquine diphosphate; chlorpromazine hydrochloride; daunomycin; daunomycinone; 5-iminodaunomycin; doxycycline; furosemide; gilvocarcin M; gilvocarcin V; hydroxychloroquine sulfate; lumidoxycycline; mefloquine hydrochloride; mequitazine; merbromin (mercurochrome); primaquine diphosphate; quinacrine dihydrochloride; quinine sulfate; and tetracycline hydrochloride, certain flavins and related compounds such as alloxazine; flavin mononucleotide; 3-hydroxyflavone; limichrome; limiflavin; 6-methylalloxazine; 7-methylalloxazine; 8-methylalloxazine; 9-methylalloxazine; 1-methyl limichrome; methyl-2-methoxybenzoate; 5-nitrosalicyclic acid; proflavine; and riboflavin, fullerenes, metalloporphyrins, metallophthalocyanines, methylene blue derivatives, naphthalimides, naphthalocyanines, certain natural compounds such as bis(4-hydroxy-3-methoxyphenyl)-1,6-heptadiene-3,5-dione; 4-(4-hydroxy-3-methoxyphenyl)-3-buten-2-one; N-formylkynurenine; kynurenic acid; kynurenine; 3-hydroxykynurenine; DL-3-hydroxykynurenine; sanguinarine; berberine; carmane; and 5,7,9(11),22-ergostatetraene-3β-ol, nile blue derivatives, NSAIDs (nonsteroidal anti-inflammatory drugs), perylenequinones, phenols, pheophorbides, pheophytins, photosensitizer dimers and conjugates, phthalocyanines, porphycenes, porphyrins, psoralens, purpurins, quinones, retinoids, rhodamines, thiophenes, verdins, vitamins and xanthene dyes (Redmond and Gamlin, *Photochem. Photobiol.*, 70(4):391–475 (1999)).

Exemplary angelicins include 3-aceto-angelicin; angelicin; 3,4'-dimethyl angelicin; 4,4'-dimethyl angelicin; 4,5'-dimethyl angelicin; 6,4'-dimethyl angelicin; 6,4-dimethyl angelicin; 4,4',5'-trimethyl angelicin; 4,4',5'-trimethyl-1'-thioangelicin; 4,6,4'-trimethyl-1'-thioangelicin; 4,6,4'-trimethyl angelicin; 4,6,5'-trimethyl-1'-thioangelicin; 6,4,4'-trimethyl angelicin; 6,4',5'-trimethyl angelicin; 4,6,4',5'-tetramethyl-1'-thioangelicin; and 4,6,4',5'-tetramethyl angelicin.

Exemplary chalcogenapyrillium dyes include pyrilium perchlorate, 4,4'-(1,3-propenyl)-bis[2,6-di(1,1-dimethylethyl)]-; pyrilium perchlorate, 2,6-bis(1,1-dimethyl-ethyl)-4-[1-[2,6-bis(1,1-dimethyl-ethyl) selenopyran-4-ylidene]-3-propenyl-; pyrilium hexofluoro phosphate, 2,6-bis-(1,1-dimethyl-ethyl)-selenopyran-4-ylidene]-3-propenyl-; pyrilium hexofluoro phosphate, 2,6-bis(1,1-dimethyl-ethyl)-selenopyran-4-ylidene]-3-propenyl-; pyrilium perchlorate, 2,6-bis(1,1-dimethyl-ethyl)-4-[1-[2,6-bis(1,1-dimethyl-ethyl)telluropyran-4-ylidene]-3-propenyl-; pyrilium hexofluoro phosphate, 2,6-bis(1,1-dimethyl-ethyl)-4-[1-[2,6-bis(1,1-dimethyl-ethyl) telluropyran-4-ylidene]-3-propenyl-; pyrilium perchlorate, 2,6-bis(1,1-dimethyl-ethyl)-4-[1-[2,6-bis-(1,1-dimethyl-ethyl)thiapyran-4-ylidene]-3-propenyl]-; selenopyrilium hexofluoro phosphate, 2,6-bis(1,1-dimethyl-ethyl)-4-[1-[2, 6-bis(1,1-dimethyl-ethyl)selenopyran-4-ylidene]-3-propenyl]-; selenopyrilium, 2,6-bis(1,1-dimethylethyl)-4-[1-[2,6-bis(1,1-dimethylethyl)selenopyran-4-ylidene]-3-propenyl]-; selenopyrilium percheorate, 2,6-bis(1,1-dimethylethyl)-4-[1-[2,6-bis(1,1-dimethylethyl)-4-[1-[2,6-bis(1,1-dimethylethyl)telluropyran-4-ylidene]-3-propenyl]-;

selenopyrilium hexofluoro phosphate, 2,6-bis(1,1-dimethyl-ethyl)-4-[1-[2,6-bis(1,1-dimethyl-ethyl)telluropyran-4-ylidene]-3-propenyl]-; selenopyrilium hexofluoro phosphate, 2,6-bis(1,1-dimethyl-ethyl)-4-[2-[2,6-bis(1,1-dimethyl-ethyl)selenopyran-4-ylidene]-4-(2-butenyl)]-; selenopyrilium hexofluoro phosphate, 2,6-bis(1,1-dimethyl-ethyl)-4-[2-[2,6-bis(1,1-dimethyl-ethyl)selenopyran-4-ylidene]-4-(2-pentenyl)]-; telluropyrilium tetrafluoroborate, 2,6-bis(1,1-dimethylethyl)-4-[1-[2,6-bis(1,1-dimethyl-ethyl)-telluropyran-4-ylidene]-3-propenyl]-; telluropyrilium hexofluoro phosphate, 2,6-bis(1,1-dimethyl-ethyl)-4-[1-[2,6-bis(1,1-dimethyl-ethyl)telluropyran-4-ylidene]-3-propenyl]-; telluropyrilium hexofluoro phosphate, 2,6-bis(1,1-dimethyl-ethyl)-4-[1-[2,6-bis(1,1-dimethyl-ethyl)telluropyran-4-ylidene]ethyl-; telluropyrilium hexofluoro phosphate, 2,6-bis(1,1-dimethyl-ethyl)-4-[1-[2,6-bis(1,1-dimethyl-ethyl)-telluropyran-4-ylidene]methyl-; thiopyrilium hexofluoro phosphate, 2,6-bis(1,1-dimethyl-ethyl)-4-[1-[2,6-bis(1,1-dimethyl-ethyl)thiopyran-4-ylidene]-3-propenyl]-; thiopyrilium hexofluoro phosphate, 2,6-bis(1,1-diethyl-ethyl)-4-[1-[2,6-bis(1,1-dimethyl-ethyl)selenopyran-4-ylidene]-3-propenyl]-; and thiopyrilium hexofluoro phosphate, 2,6-bis(1,1-dimethyl-ethyl)-4-[1-[2,6-bis(1,1-dimethyl-ethyl)telluropyran-4-ylidene]-3-propenyl]-.

Exemplary chlorins dyes include 5-azachlorin dimethyl ester derivative;. 5,10,15,20-tetrakis-(m-hydroxyphenyl)bacteriochlorin; benzoporphyrin derivative monoacid ring A; benzoporphyrin derivative monoacid ring-A; porphine-2,18-dipropanoic acid, 7-[2-dimethyl-amino)-2-oxoethyl]-8-ethylidene-7,8-dihydro-3,7,12,17-tetramethyl, dimethyl-ester; porphine-2,18-dipropanoic acid, 7-[2-dimethyl-amino)-2-oxoethyl]-8-ethylidene-8-ethyl-7,8-dihydro-3,7,12,17-tetramethyl, dimethylester Z; porphine-2,18-dipropanoic acid, 7-[2-dimethyl-amino)-2-oxoethyl]-8-ethylidene-8-ethyl-7,8-dihydro-3,7,12,17-tetramethyl, dimethylester Z ECHL; porphine-2,18-dipropanoic acid, 7-[2-dimethyl-amino)-2-oxoethyl]-8-ethylidene-8-n-heptyl-7,8-dihydro-3,7,12,17-tetramethyl, dimethylester Z; tin(II) porphine-2,18-dipropanoic acid, 7-[2-(dimethylamino-2-oxoethyl]-8-ethylidene-8-n-heptyl-7,8-dihydro-3,7,12,17-tetramethyl, dimethylester Z; chlorin $e_6$; chlorin $e_6$ dimethyl ester; chlorin $e_6$ $k_3$; chlorin $e_6$ monomethyl ester; chlorin $e_6$ $Na_3$; chlorin $p_6$; chlorin $p_6$-trimethylester; chlorin derivative zinc(II)porphine-2,18-dipropanoic acid, 7-[2-(dimethylamino)-2-oxoethyl]-8-ethylidene-8-n-heptyl-7,8-dihydro-3,7,12,17-tetramethyl, dimethylester Z; $13^1$-deoxy-20-formyl-vic-dihydroxy-bacteriochlorin di-tert-butyl aspartate; $13^1$-deoxy-20-formyl-4-keto-bacteriochlorin di-tert-butyl aspartate; di-L-aspartyl chlorin $e_6$; mesochlorin; 5,10,15,20-tetrakis-(m-hydroxyphenyl)chlorin; meta-(tetrahydroxyphenyl)chlorin; methyl-$13^1$-deoxy-20-formyl-4-keto-bacteriochlorin; mono-L-aspartyl chlorin $e_6$; photoprotoporphyrin IX dimethyl ester; phycocyanobilin dimethyl ester; protochlorophyllide a; tin(IV)chlorin $e_6$; tin chlorin $e_6$; tin L-aspartyl chlorin $e_6$; tin octaethylbenzochlorin; tin(IV)chlorin; zinc chlorin $e_6$; and zinc L-aspartyl chlorin $e_6$.

Exemplary chlorophylls dyes include chlorophyll a; chlorophyll b; oil soluble chlorophyll; bacteriochlorophyll a; bacteriochlorophyll b; bacteriochlorophyll c; bacteriochlorophyll d; protochlorophyll; protochlorophyll a; amphiphilic chlorophyll derivative 1; and amphiphilic chlorophyll derivative 2.

Exemplary coumarins include 3-benzoyl-7-methoxycoumarin; 7-diethylamino-3-thenoylcoumarin; 5,7-dimethoxy-3-(1-naphthoyl)coumarin; 6-methylcoumarin; 2H-selenolo[3,2-g][1]benzopyran-2-one; 2H-selenolo[3,2-g][1]benzothiopyran-2-one; 7H-selenolo[3,2-g][1]benzoseleno-pyran-7-one; 7H-selenopyrano[3,2-f][1]benzofuran-7-one; 7H-selenopyrano[3,2-f][1]benzothiophene-7-one; 2H-thienol[3,2-g][1-benzopyran-2-one; 7H-thienol[3,2-g][1]benzothiopyran-7-one; 7H-thiopyrano[3,2-f][1]benzofuran-7-one; coal tar mixture; khellin; RG 708; RG277; and visnagin.

Exemplary cyanines include benzoselenazole dye; benzoxazole dye; 1,1'-diethyloxacarbocyanine; 1,1'-diethyloxadicarbocyanine; 1,1'-diethylthiacarbocyanine; 3,3'-dialkylthiacarbocyanines(n=2–18); 3,3'-diethylthiacarbocyanine iodide; 3,3'-dihexylselenacarbocyanine; kryptocyanine; MC540 benzoxazole derivative; MC540 quinoline derivative; merocyanine 540; and meso-ethyl, 3,3'-dihexylselenacarbocyanine.

Exemplary fullerenes include $C_{60}$; $C_{70}$; $C_{76}$; dihydrofullerene; 1,9-(4-hydroxy-cyclohexano)-buckminsterfullerene; [1-methyl-succinate-4-methyl-cyclohexadiene-2, 3]-buckminster-fullerene; and tetrahydro fullerene.

Exemplary metalloporphyrins include cadmium(II)chlorotexaphyrin nitrate; cadmium(II)meso-diphenyl tetrabenzoporphyrin; cadmium meso-tetra-(4-N-methylpyridyl)-porphine; cadmium(II)texaphyrin; cadmium(II)texaphyrin nitrate; cobalt meso-tetra-(4-N-methylpyridyl)-porphine; cobalt(II)meso(4-sulfonatophenyl)-porphine; copper hematoporphyrin; copper meso-tetra-(4-N-methylpyridyl)-porphine; copper(II)meso(4-sulfonatophenyl)-porphine; Europium(III)dimethyltexaphyrin dihydroxide; gallium tetraphenylporphyrin; iron meso-tetra(4-N-methylpyridyl)-porphine; lutetium(III)tetra(N-methyl-3-pyridyl)-porphyrin chloride; magnesium(II)meso-diphenyl tetrabenzoporphyrin; magnesium tetrabenzoporphyrin; magnesium tetraphenylporphyrin; magnesium(II)meso(4-sulfonatophenyl)-porphine; magnesium(II)texaphyrin hydroxide metalloporphyrin; magnesium meso-tetra-(4-N-methylpyridyl)-porphine; manganese meso-tetra-(4-N-methylpyridyl)-porphine; nickel meso-tetra(4-N-methylpyridyl)-porphine; nickel(II)meso-tetra(4-sulfonatophenyl)-porphine; palladium(II)meso-tetra-(4-N-methylpyridyl)-porphine; palladium meso-tetra-(4-N-methylpyridyl)-porphine; palladium tetraphenylporphyrin; palladium(II)meso(4-sulfonatophenyl)-porphine; platinum (II)meso(4-sulfonatophenyl)-porphine; samarium(II) dimethyltexaphyrin dihydroxide; silver(II)meso(4-sulfonatophenyl)-porphine; tin(IV)protoporphyrin; tin meso-tetra-(4-N-methylpyridyl)-porphine; tin meso-tetra(4-sulfonatophenyl)-porphine; tin(IV)tetrakis(4-sulfonatophenyl)porphyrin dichloride; zinc(II)15-aza-3,7,12,18-tetramethyl-porphyrinato-13,17-diyl-dipropionic acid-dimethylester; zinc(II)chlorotexaphyrin chloride; zinc coproporphyrin III; zinc(II)2,11,20,30-tetra-(1,1-dimethyl-ethyl)tetranaphtho(2,3-b:2',3'-g:2"3"-1:2'"3'"-q) porphyrazine; zinc(II)2-(3-pyridyloxy)benzo[b]-10,19,28-tri(1,1-dimethylethyl)trinaphtho[2',3'-g:2"3"1::2"',3'"-q] porphyrazine; zinc(II)2,18-bis-(3-pyridyloxy)dibenzo[b,l]-10,26-di(1,1-dimethyl-ethyl)dinaphtho[2',3'-g:2'",3'"-q] porphyrazine; zinc(II)2,9-bis-(3-pyridyloxy)dibenzo[b,g]-17,26-di(1,1-dimethyl-ethyl)dinaphtho[2",3"-1:2'",3'"-q] porphyrazine; zinc(II)2,9,16-tris-(3-pyridyloxy)tribenzo[b, g,l]-24=(1,1-dimethyl-ethyl)naphtho[2'",3'"-q] porphyrazine; zinc(II)2,3-bis-(3-pyridyloxy)benzo[b]-10, 19,28-tri(1.1-dimethyl-ethyl)trinaphtho[2',3'-g:2",3"1:2'", 3'"-q]porphyrazine; zinc(II)2,3,18,19-tetrakis-(3-pyridyloxy)dibenzo[b,l]-10,26-di(1,1-dimethyl-ethyl) trinaphtho[2',3'-g:2'",3'"-q]porphyrazine; zinc(II)2,3,9,10-tetrakis-(3-pyridyloxy) dibenzo[b,g]-17,26-di(1,1-dimethylethyl)dinaphtho[2″,3″-1:2‴,3‴-q]porphyrazine; zinc (II)2,3, 9,10,16,17-hexakis-(3-pyridyloxy)tribenzo[b,g,l]-24-(1,1-dimethyl-ethyl)naphtho[2‴,3‴-q]porphyrazine; zinc(II)2-(3-N-methyl)pyridyloxy)benzo[b]-10,19,28-tri(1,1-dimethyl-ethyl)trinaphtho[2′,3′-g:2″,3‴″1:2‴,3‴-q] porphyrazine monoiodide; zinc(II)2,18-bis-(3-(N-methyl) pyridyloxy)dibenzo[b,l]-10,26-di(1,1-dimethylethyl) dinaphtho[2′,3′-g:2‴,3‴-q]porphyrazine diiodide; zinc(II)2, 9-bis-(3-(N-methyl)pyridyloxy)dibenzo[b,g]-17,26-di(1,1-dimethylethyl)dinaphtho[2″,3″-1:2‴,3‴-q]porphyrazine diiodide; zinc(II)2,9,16-tris-(3-(N-methyl-pyridyloxy) tribenzo[b,g,l]-24-(1,1-dimethylethyl)naphtho[2‴,3‴-q] porphyrazine triiodide; zinc(II)2,3-bis-(3-(N-methyl) pyridyloxy)benzo[b]-10,19,28-tri(1,1-dimethylethyl) trinaphtho[2′,3′-g:2″,3″-1:2‴,3‴-q]porphyrazine diiodide; zinc(II)2,3,18,19-tetrakis-(3-(N-methyl)pyridyloxy)dibenzo [b,l]-10,26-di(1,1-dimethyl)dinaphtho[2′,3′-g:2‴,3‴-q] porphyrazine tetraiodide; zinc(II)2,3,9,10-tetrakis-(3-(N-methyl)pyridyloxy)dibenzo[g,g]-17,26-di(1,1-dimethylethyl)dinaphtho[2″,3″-1:2‴,3‴-q]porphyrazine tetraiodide; zinc(II)2,3,9,10,16,17-hexakis-(3-(N-methyl) pyridyloxy)tribenzo[b,g,l]-24-(1,1-dimethylethyl)naphtho [2‴,3‴-q]porphyrazine hexaiodide; zinc(II)meso-diphenyl tetrabenzoporphyrin; zinc(II)meso-triphenyl tetrabenzoporphyrin; zinc(II)meso-tetrakis(2,6-dichloro-3-sulfonatophenyl)porphyrin; zinc(II)meso-tetra-(4-N-methylpyridyl)-porphine; zinc(II)5,10,15,20-meso-tetra(4-octyl-phenylpropynyl)-porphine; zinc porphyrin c; zinc protoporphyrin; zinc protoporphyrin IX; zinc(II)meso-triphenyl-tetrabenzoporphyrin; zinc tetrabenzoporphyrin; zinc(II)tetrabenzoporphyrin; zinc tetranaphthaloporphyrin; zinc tetraphenylporphyrin; zinc(II)5,10,15,20-tetraphenylporphyrin; zinc(II)meso(4-sulfonatophenyl)-porphine; and zinc(II)texaphyrin chloride.

Exemplary metallophthalocyanines include aluminum mono-(6-carboxy-pentyl-amino-sulfonyl)-trisulfophthalocyanine; aluminum di-(6-carboxy-pentyl-amino-sulfonyl)-trisulfophthalocyanine; aluminum(III)octa-n-butoxy phthalocyanine; aluminum phthalocyanine; aluminum(III)phthalocyanine disulfonate; aluminum phthalocyanine disulfonate; aluminum phthalocyanine disulfonate(cis isomer); aluminum phthalocyanine disulfonate(clinical prep.); aluminum phthalocyanine phthalimido-methyl sulfonate; aluminum phthalocyanine sulfonate; aluminum phthalocyanine trisulfonate; aluminum (III)phthalocyanine trisulfonate; aluminum(III) phthalocyanine tetrasulfonate; aluminum phthalocyanine tetrasulfonate; chioroaluminum phthalocyaninet chloroaluminum phthalocyanine sulfonate; chloroaluminum phthalocyanine disulfonate; chloroaluminum phthalocyanine tetrasulfonate; chloroaluminum-t-butyl-phthalocyanine; cobalt phthalocyanine sulfonate; copper phthalocyanine sulfonate; copper(II)tetra-carboxy-phthalocyanine; copper(II)-phthalocyanine; copper t-butyl-phthalocyanine; copper phthalocyanine sulfonate; copper(II)tetrakis-[methylene-thio[(diimethyl-hamino)methylidyne]]phthalocyanine tetrachloride; dichlorosilicon phthalocyanine; gallium(III)octa-n-butoxy phthalocyanine; gallium(II)phthalocyanine disulfonate; gallium phthalocyanine disulfonate; gallium phthalocyanine tetrasulfonate-chloride; gallium(II) phthalocyanine tetrasulfonate; gallium phthalocyanine trisulfonate-chloride; gallium(II)phthalocyanine trisulfonate; $GaPcS_1tBu_3$; $GaPcS_2tBu_2$; $GaPcS_3tBu_1$; germanium (IV)octa-n-butoxy phthalocyanine; germanium phthalocyanine derivative; silicon phthalocyanine derivative; germanium(IV)phthalocyanine octakis-alkoxy-derivatives; iron phthalocyanine sulfonate; lead(II)2,3,9,10,16,17,23,24-octakis(3,6-dioxaheptyloxy)phthalocyanine; magnesium t-butyl-phthalocyanine; nickel(II)2,3,9,10,16,17,23,24-octakis(3,6-dioxaheptyloxy)phthalocyanine; palladium(II) octa-n-butoxy phthalocyanine; palladium(II)tetra(t-butyl)-phthalocyanine; (diol)(t-butyl)$_3$-phthalocyanato palladium (II); ruthenium(II)dipotassium[bis(triphenyl-phosphine-monosulphonate)phthalocyanine; silicon phthalocyanine bis (tri-n-hexyl-siloxy)-; sllicon phthalocyanine bis(tri-phenyl-siloxy)-; $HOSiPcOSi(CH_3)_2(CH_2)_3N(CH_3)_2$; $HOSiPcOSi(CH_3)_2(CH_2)_3N(CH_2CH_3)_2$; $SiPc[OSi(CH_3)_2(CH_2)_3N(CH_3)_2]_2$; $SiPc[OSi(CH_3)_2(CH_2)_3N(CH_2CH_3)(CH_2)_2N(CH_3)_2]_2$; tin(IV)octa-n-phthalocyanine; vanadium phthalocyanine sulfonate; zinc(II)octa-n-butoxy phthalocyanine; zinc(II)2,3,9,10,16,17,23,24-octakis(2-ethoxy-ethoxy)phthalocyanine; zinc(II)2,3,9,10,16,17,23,24-octakis(3,6-dioxaheptyloxy)phthalocyanine; zinc(II)1,4,8, 11,15,18,22,25-octa-n-butoxy-phthalocyanine; zn(II)-phthalocyanine-octabutoxy; zn(II)-phthalocyanine; zinc phthalocyanine; zinc(II)phthalocyanine; zinc phthalocyanine and perdeuterated zinc phthalocyanine; zinc(II) phthalocyanine disulfonate; zinc phthalocyanine disulfonate; zinc phthalocyanine sulfonate; zinc phthalocyanine tetrabromo-; zinc(II)phthalocyanine tetra-t-butyl-; zinc(II) phthalocyanine tetra-(t-butyl)-; zinc phthalocyanine tetracarboxy-; zinc phthalocyanine tetrachloro-; zinc phthalocyanine tetrahydroxyl; zinc phthalocyanine tetraiodo-; zinc((I)tetrakis-(1,1-dimethyl-2-phthalimido)ethyl phthalocyanine; zinc(II)tetrakis-(1,1-dimethyl-2-amino)-ethyl-phthalocyanine; zinc(II)phthalocyanine tetrakis(1,1-dimethyl-2-trimethyl ammonium)ethyl tetraiodide; zinc phthalocyanine tetrasulphonate; zinc phthalocyanine tetrasulfonate; zinc(II)phthalocyanine tetrasulfonate; zinc(II) phthalocyanine trisulfonate; zinc phthalocyanine trisulfonate; zinc(II)(t-butyl)$_3$-phthalocyanine diol; zinc tetradibenzobarreleno-octabutoxy-phthalocyanine; zinc(II) 2,9,16,23,-tetrakis-(3-(N-methyl)pyridyloxy) phthalocyanine tetraiodide; and zinc(II)2,3,9,10,16,17,23, 24-octakis-(3-(N-methyl)pyridyloxy)phthalocyanine complex octaiodide; and zinc(II)2,3,9,10,16,17,23,24-octakis-(3-pyridyloxy)phthalocyanine.

Exemplary methylene blue derivatives include 1-methyl methylene blue; 1,9-dimethyl methylene blue; methylene blue; methylene blue (16 μM); methylene blue (14 μM); methylene violet; bromomethylene violet; 4-iodomethylene violet; 1,9-dimethyl-3-dimethyl-amino-7-diethyl-amino-phenothiazine; and 1,9-dimethyl-3-diethylamino-7-dibutyl-amino-phenothiazine.

Exemplary naphthalimides blue derivatives include N,N′-bis-(hydroperoxy-2-methoxyethyl)-1,4,5,8-naphthaldiimide; N-(hydroperoxy-2-methoxyethyl)-1,8-naphthalimide; 1,8-naphthalimide; N,N′-bis(2,2-dimethoxyethyl)-1,4,5,8-naphthaldiimide; and N,N′-bis(2,2-dimethylpropyl)-1,4,5,8-naphthaldiimide.

Exemplary naphthalocyanines include aluminum t-butyl-chloronaphthalocyanine; silicon bis (dimethyloctadecylsiloxy)2,3-naphthalocyanine; silicon bis (dimethyloctadecylsiloxy)naphthalocyanine; silicon bis (dimethylthexylsiloxy)2,3-naphthalocyanine; silicon bis (dimethylthexylsiloxy)naphthalocyanine; silicon bis(t-butyldimethylsiloxy)2,3-naphthalocyanine; silicon bis(tert-butyldimethylsiloxy)naphthalocyanine; silicon bis(tri-n-hexylsiloxy)2,3-naphthalocyanine; silicon bis(tri-n-hexylsiloxy)naphthalocyanine; silicon naphthalocyanine; t-butylnaphthalocyanine; zinc (II)naphthalocyanine; zinc(II) tetraacetyl-amidonaphthalocyanine; zinc(II) tetraaminonaphthalocyanine; zinc(II) tetrabenzamidonaphthalocyanine; zinc(II)

tetrahexylamidonaphthalocyanine; zinc(II)tetramethoxybenzamidonaphthalocyanine; zinc(II) tetramethoxynaphthalocyanine; zinc naphthalocyanine tetrasulfonate; and zinc(II) tetradodecylamidonaphthalocyanine.

Exemplary nile blue derivatives include benzo[a]phenothiazinium, 5-amino-9-diethylamino-; benzo[a]phenothiazinium, 5-amino-9-diethylamino-6-iodo-; benzo[a]phenothiazinium, 5-benzylamino-9-diethylamino-; benzo[a]phenoxazinium, 5-amino-6,8-dibromo-9-ethylamino-; benzo[a]phenoxazinium, 5-amino-6,8-diiodo-9-ethylamino-; benzo[a]phenoxazinium, 5-amino-6-bromo-9-diethylamino-; benzo[a]phenoxazinium, 5-amino-9-diethylamino-(nile blue A); benzo[a]phenoxazinium, 5-amino-9-diethylamino-2,6-diiodo-; benzo[alphenoxazinium, 5-amino-9-diethylamino-2,-iodo; benzo[a]phenoxazinium, 5-amino-9-diethylamino-6-iodo-; benzo[a]phenoxazinium, 5-benzylamino-9-diethylamino-(nile blue 2B); 5-ethylamino-9-diethylamino-benzo[a]phenoselenazinium chloride; 5-ethylamino-9-diethyl-aminobenzo[a]phenothiazinium chloride; and 5-ethylamino-9-diethyl-aminobenzo[a]phenoxazinium chloride.

Exemplary NSAIDs (nonsteroidal anti-inflammatory drugs) include benoxaprofen; carprofen; carprofen dechlorinated(2-(2-carbazolyi)propionic acid); carprofen(3-chlorocarbazole); chlorobenoxaprofen; 2,4-dichlorobenoxaprofen; cinoxacin; ciprofloxacin; decarboxy-ketoprofen; decarboxy-suprofen; decarboxy-benoxaprofen; decarboxy-tiaprofenic acid; enoxacin; fleroxacin; fleroxacin-N-oxide; flumequine; indoprofen; ketoprofen; lomelfloxacin; 2-methyl-4-oxo-2H-1,2-benzothiazine-1,1-dioxide; N-demethyl fleroxacin; nabumetone; nalidixic acid; naproxen; norfloxacin; ofloxacin; pefloxacin; pipemidic acid; piroxicam; suprofen; and tiaprofenic acid.

Exemplary perylenequinones include hypericins such as hypericin; hypericin monobasic sodium salt; di-aluminum hypericin; di-copper hypericin; gadolinium hypericin; terbium hypericin, hypocrellins such as acetoxy hypocrellin A; acetoxy hypocrellin B; acetoxy iso-hypocrellin A; acetoxy iso-hypocrellin B; 3,10-bis[2-(2-aminoethylamino)ethanol] hypocrellin B; 3,10-bis[2-(2-aminoethoxy)ethanol] hypocrellin B; 3,1 0-bis[4-(2-aminoethyl)morpholine] hypocrellin B; n-butylaminated hypocrellin B; 3,10-bis(butylamine)hypocrellin B; 4,9-bis(butylamine)hypocrellin B; carboxylic acid hypocrellin B; cystamine-hypocrellin B; 5-chloro hypocrellin A or 8-chloro hypocrellin A; 5-chloro hypocrellin B or 8-chloro hypocrellin B; 8-chloro hypocrellin B; 8-chloro hypocrellin A or 5-chloro hypocrellin A; 8-chloro hypocrellin B or 5-chloro hypocrellin B; deacetylated aldehyde hypocrellin B; deacetylated hypocrellin B; deacetylated hypocrellin A; deacylated, aldehyde hypocrellin B; demethylated hypocrellin B; 5,8-dibromo hypocrellin A; 5,8-dibromo hypocrellin B; 5,8-dibromo iso-hypocrellin B; 5,8-dibromo[1,12-CBr=CMeCBr(COMe)]hypocrellin B; 5,8-dibromo[1,12-CHBrC(=CH$_2$)CBr(COMe)] hypocrellin B; 5,8-dibromo[1-CH$_2$COMe, 12-COCOCH$_2$Br—]hypocrellin B; 5,8-dichloro hypocrellin A; 5,8-dichloro hypocrellin B; 5,8-dichlorodeacytylated hypocrellin B; 5,8-diiodo hypocrellin A; 5,8-diiodo hypocrellin B; 5,8-diiodo[1,12-CH=CMeCH(COCH$_2$I$_2$)—] hypocrellin B; 5,8-diiodo[1,12-CH$_2$C(CH$_2$I)=C(COMe)—]hypocrellin B; 2-(N,N-diethylamino) ethylaminated hypocrellin B; 3,10-bis[2-(N,N-diethylamino)-ethylamine]hypocrellin B; 4,9-bis[2-(N,N-diethyl-amino)-ethylamine]iso-hypocrellin B; dihydro-1,4-thiazine carboxylic acid hypocrellin B; dihydro-1,4-thiazine hypocrellin B; 2-(N,N-dimethylamino)propylamine hypocrellin B; dimethyl-1,3,5,8,10,12-hexamethoxy-4,9-perylenequinone-6,7-diacetate; dimethyl-5,8-dihydroxy-1,3,10,13-tetramethoxy-4,9-perylenequinone-6,7-diacetate; 2,11-dione hypocrellin A; ethanolamine hypocrellin B; ethanolamine iso-hypocrellin B; ethylenediamine hypocrellin B; 11-hydroxy hypocrellin B or 2-hydroxy hypocrellin B; hypocrellin A; hypocrellin B; 5-iodo[1,12-CH$_2$C(CH$_2$I)=C (COMe)—]hypocrellin B; 8-iodo[1,12-CH$_2$C(CH$_2$I)=C (COMe)—]hypocrellin B; 9-methylamino iso-hypocrellin B; 3,10-bis[2-(N,N-methylamino)propylamine]hypocrellin B; 4,9-bis(methylamine iso-hypocrellin B; 14-methylamine iso-hypocrellin B; 4-methylamine iso-hypocrellin B; methoxy hypocrellin A; methoxy hypocrellin B; methoxy iso-hypocrellin A; methoxy iso-hypocrellin B; methylamine hypocrellin B; 2-morpholino ethylaminated hypocrellin B; pentaacetoxy hypocrellin A; PQP derivative; tetraacetoxy hypocrellin B; 5,8,15-tribromo hypocrellin B; calphostin C, Cercosporins such as acetoxy cercosporin; acetoxy iso-cercosporin; aminocercosporin; cercosporin; cercosporin+iso-cercosporin(1/1 molar); diaminocercosporin; dimethylcercosporin; 5,8-dithiophenol cercosporin; iso-cercosporin; methoxycercosporin; methoxy iso-cercosporin; methylcercosporin; noranhydrocercosporin; elsinochrome A; elsinochrome B; phleichrome; and rubellin A.

Exemplary phenols include 2-benzylphenol; 2,2'-dihydroxybiphenyl; 2,5-dihydroxybiphenyl; 2-hydroxybiphenyl; 2-methoxybiphenyl; and 4-hydroxybiphenyl.

Exemplary pheophorbides include pheophorbide a; methyl 13$^1$-deoxy-20-formyl-7,8-vic-dihydro-bacterio-meso-pheophorbide a; methyl-2-(1-dodecyloxyethyl)-2-devinyl-pyropheophorbide a; methyl-2-(1-heptyl-oxyethyl)-2-devinyl-pyropheophorbide a; methyl-2-(1-hexyl-oxyethyl)-2-devinyl-pyropheophorbide a; methyl-2-(1-methoxy-ethyl)-2-devinyl-pyropheophorbide a; methyl-2-(1-pentyl-oxyethyl)-2-devinyl-pyropheophorbide a; magnesium methyl bacteriopheophorbide d; methyl-bacteriopheophorbide d; and pheophorbide.

Exemplary pheophytins include bacteriopheophytin a; bacteriopheophytin b; bacteriopheophytin c; bacteriopheophytin d; 10-hydroxy pheophytin a; pheophytin; pheophytin a; and protopheophytin.

Exemplary photosensitizer dimers and conjugates include aluminum mono-(6-carboxy-pentyl-amino-sulfonyl)-trisulfophthalocyanine bovine serum albumin conjugate; dihematoporphyrin ether(ester); dihematoporphyrin ether; dihematoporphyrin ether (ester)-chlorin; hematoporphyrin-chlorin ester; hematoporphyrin-low density lipoprotein conjugate; hematoporphyrin-high density lipoprotein conjugate; porphine-2,7,18-tipropanoic acid, 13,13'-(1,3-propanediyl) bis[3,8,12,17-tetramethyl]-; porphine-2,7,18-tripropanoic acid, 13,13'-(1,11-undecanediyl)bis[3,8,12,17-tetramethyl]-; porphine-2,7,18-tripropanoic acid, 13,13'-(1,6-hexanediyl) bis[3,8,12,17-tetramethyl]-; SnCe6-MAb conjugate 1.7:1; SnCe6-MAb conjugate 1.7:1; SnCe6-MAb conjugate 6.8:1; SnCe6-MAb conjugate 11.2:1; SnCe6-MAb conjugate 18.9:1; SnCe6-dextran conjugate 0.9:1; SnCe6-dextran conjugate 3.5:1; SnCe6-dextran conjugate 5.5:1; SnCe6-dextran conjugate 9.9:1; α-terthienyl-bovine serum albumin conjugate(12:1); α-terthienyl-bovine serum albumin conjugate(4:1); and tetraphenylporphine linked to 7-chloroquinoline.

Exemplary phthalocyanines include (diol)(t-butyl)$_3$-phthalocyanine; (t-butyl)$_4$-phthalocyanine; cis-octabutoxy-dibenzo-dinaphtho-porphyrazine; trans-octabutoxy-dibenzo-dinaphtho-porphyrazine; 2,3,9,10,16,17,23,24- octakis2-ethoxyethoxy) phthalocyanine; 2,3,9,10,16,17,23, 24-octakis(3,6-dioxaheptyloxy)phthalocyanine; octa-n-butoxy phthalocyanine; phthalocyanine; phthalocyanine sulfonate; phthalocyanine tetrasulphonate; phthalocyanine tetrasulfonate; t-butyl-phthalocyanine; tetra-t-butyl phthalocyanine; and tetradibenzobarreleno-octabutoxy-phthalocyanine.

Exemplary porphycenes include 2,3-($2^3$-carboxy-$2^4$-methoxycarbonyl benzo)-7,12,17-tris(2-methoxyethyl) porphycene; 2-(2-hydroxyethyl)-7,12,17-tri(2-methoxyethyl)porphycene; 2-(2-hydroxyethyl)-7,12,17-tri-n-propyl-porphycene; 2-(2-methoxyethyl)-7,12,17-tri-n-propyl-porphycene; 2,7,12,17-tetrakis(2-methoxyethyl) porphycene; 2,7,12,17-tetrakis(2-methoxyethyl)-9-hydroxy-porphycene; 2,7,12,17-tetrakis(2-methoxyethyl)-9-methoxy-porphycene; 2,7,12,17-tetrakis(2-methoxyethyl)-9-n-hexyloxy-porphycene; 2,7,12,17-tetrakis(2-methoxyethyl)-9-acetoxy-porphycene; 2,7,12,17-tetrakis(2-methoxyethyl)-9-caproyloxy-porphycene; 2,7,12,17-tetrakis(2-methoxyethyl)-9-pelargonyloxy-porphycene; 2,7,12,17-tetrakis(2-methoxyethyl)-9-stearoyloxy-porphycene; 2,7,12,17-tetrakis(2-methoxyethyl)-9-(N-t-butoxycarbonylglycinoxy)porphycene; 2,712,17-tetrakis(2-methoxyethyl)-9-[4-(($\beta$-apo-7-carotenyl)benzoyloxyl-porphycene; 2,7,12,17-tetrakis(2-methoxyethyl)-9-amino-porphycene; 2,7,12,17-tetrakis(2-methoxyethyl)-9-acetamido-porphycene; 2,7,12,17-tetrakis(2-methoxyethyl)-9-glutaramido-porphycene; 2,7,12,17-tetrakis(2-methoxyethyl)-9-(methyl-glutaramido)-porphycene; 2,7,12,17-tetrakis(2-methoxyethyl)-9-(glutarimido)-porphycene; 2,7,12,17-tetrakis(2-methoxyethyl)-3-(N,N-dimethylaminomethyl) porphycene; 2,7,12,17-tetrakis(2-methoxyethyl)-3-(N,N-dimethylaminomethyl)-porphycene hydrochloride; 2,7,12,17-tetrakis(2-ethoxyethyl)-porphycene; 2,7,12,17-tetra-n-propyl-porphycene; 2,7,12,17-tetra-n-propyl-9-hydroxy-porphycene; 2,7,12,17-tetra-n-propyl-9-methoxy-porphycene; 2,7,12,17-tetra-n-propyl-9-acetoxy porphycene; 2,7,12,17-tetra-n-propyl-9-(t-butyl glutaroxy)-porphycene; 2,7,12,17-tetra-n-propyl-9-(N-t-butoxycarbonylglycinoxy)-porphycene; 2,7,12,17-tetra-n-propyl-9-(4-N-t-butoxy-carbonyl-butyroxy)-porphycene; 2,7,12,17-tetra-n-propyl-9-amino-porphycene; 2,7,12,17-tetra-n-propyl-9-acetamido-porphycene; 2,7,12,17-tetra-n-propyl-9-glutaramido-porphycene; 2,7,12,17-tetra-n-propyl-9-(methyl glutaramido)-porphycene; 2,7,12,17-tetra-n-propyl-3-(N,N-dimethylaminomethyl)porphycene; 2,7,12,17-tetra-n-propyl-9,10-benzo porphycene; 2,7,12,17-tetra-n-propyl-9-p-benzoyl carboxy-porphycene; 2,7,12,17-tetra-n-propyl-porphycene; 2,7,12,17-tetra-t-butyl-3,6;13,16-dibenzo-porphycene; 2,7-bis(2-hydroxyethyl)-12,17-di-n-propyl-porphycene; 2,7-bis(2-methoxyethyl)-12,17-di-n-propyl-porphycene; and porphycene.

Exemplary porphyrins include 5-azaprotoporphyrin dimethylester; bis-porphyrin; coproporphyrin III; coproporphyrin III tetramethylester; deuteroporphyrin; deuteroporphyrin IX dimethylester; diformyldeuteroporphyrin IX dimethylester; dodecaphenylporphyrin; hematoporphyrin; hematoporphyrin (8 $\mu$M); hematoporphyrin (400 $\mu$M); hematoporphyrin (3 $\mu$M); hematoporphyrin (18 $\mu$M); hematoporphyrin (30 $\mu$M); hematoporphyrin (67 $\mu$M); hematoporphyrin (150 $\mu$M); hematoporphyrin IX; hematoporphyrin monomer; hematoporphyrin dimer; hematoporphyrin derivative; hematoporphyrin derivative (6 $\mu$M); hematoporphyrin derivative (200 $\mu$M); hematoporphyrin derivative A (20 $\mu$); hematoporphyrin IX dihydrochloride; hematoporphyrin dihydrochloride; hematoporphyrin IX dimethylester; haematoporphyrin IX dimethylester; miesoporphyrin dimethylester; mesoporphyrin IX dimethylester; monoformyl-monovinyl-deuteroporphyrin IX dimethylester; monohydroxyethylvinyl deuteroporphyrin; 5,10,15,20-tetra (o-hydroxyphenyl)porphyrin; 5,10,15,20-tetra(m-hydroxyphenyl)porphyrin; 5,10,15,20-tetrakis-(m-hydroxyphenyl)porphyrin; 5,10,15,20-tetra(p-hydroxyphenyl)porphyrin; 5,10,15,20-tetrakis(3-methoxyphenyl)porphyrin; 5,10,15,20-tetrakis(3,4-dimethoxyphenyl)porphyrin; 5,10,15,20-tetrakis(3,5-dimethoxyphenyl)porphyrin; 5,10,15,20-tetrakis(3,4,5-trimethoxyphenyl)porphyrin; 2,3,7,8,12,13,17,18-octaethyl-5,10,15,20-tetraphenylporphyrin; Photofrin®; Photofrin® II; porphyrin c; protoporphyrin; protoporphyrin IX; protoporphyrin dimethylester; protoporphyrin IX dimethylester; protoporphyrin propylanminoethylformamide iodide; protoporphyrin N,N-dimethylaminopropylformamide; protoporphyrin propylaminopropylformamide iodide; protoporphyrin butylformamide; protoporphyrin N,N-dimethylaminoformamide; protoporphyrin formamide; sapphyrin 1 3,12,13,22-tetraethyl-2,7,18,23 tetramethyl sapphyrin-8,17-dipropanol; sapphyrin 2 3,12,13,22-tetraethyl-2,7,18,23 tetramethyl sapphyrin-8-monoglycoside; sapphyrin 3; meso-tetra-(4-N-carboxyphenyl)-porphine; tetra-(3-methoxyphenyl)-porphine; tetra-(3-methoxy-2,4-difluorophenyl)-porphine; 5,10,15,20-tetrakis(4-N-methylpyridyl)porphine; meso-tetra-(4-N-methylpyridyl)-porphine tetrachloride; meso-tetra(4-N-methylpyridyl)-porphine; meso-tetra-(3-N-methylpyridyl)-porphine; meso-tetra-(2-N-methylpyridyl)-porphine; tetra(4-N,N,N-trimethylanilinium)porphine; mieso-tetra-(4-N,N,N"-trimethylamino-phenyl)porphine tetrachloride; tetranaphthaloporphyrin; 5,10,15,20-tetraphenylporphyrin; tetraphenylporphyrin; meso-tetra-(4-N-sulfonatophenyl)-porphine; tetraphenylporphine tetrasulfonate; meso-tetra(4-sulfonatophenyl)porphine; tetra(4-sulfonatophenyl) porphine; tetraphenylporphyrin sulfonate; meso-tetra(4-sulfonatophenyl)porphine; tetrakis(4-sulfonatophenyl) porphyrin; meso-tetra(4-sulfonatophenyl)porphine; meso(4-sulfonatophenyl)porphine; meso-tetra(4-sulfonatophenyl) porphine; tetrakis(4-sulfonatophenyl)porphyrin; meso-tetra (4-N-trimethylanilinium)-porphine; uroporphyrin; uroporphyrin I (17 $\mu$M); uroporphyrin IX; and uroporphyrin I (18 $\mu$M).

Exemplary psoralens include psoralen; 5-methoxypsoralen; 8-methoxypsoralen; 5,8-dimethoxypsoralen; 3-carbethoxypsoralen; 3-carbethoxy-pseudopsoralen; 8-hydroxypsoralen; pseudopsoralen; 4,5',8-trimethylpsoralen; allopsoralen; 3-aceto-allopsoralen; 4,7-dimethyl-allopsoralen; 4,7,4'-trimethyl-allopsoralen; 4,7,5'-trimethyl-allopsoralen; isopseudopsoralen; 3-acetoisopseudopsoralen; 4,5'-dimethyl-isopseudopsoralen; 5',7-dimethyl-isopseudopsoralen; pseudoisopsoralen; 3-acetopseudoisopsoralen; 3/4',5'-trimethyl-aza-psoralen; 4,4',8-trimethyl-5'-amino-methylpsoralen; 4,4',8-trimethyl-phthalamyl-psoralen; 4,5',8-trimethyl-4'-aminomethyl psoralen; 4,5',8-trimethyl-bromopsoralen; 5-nitro-8-methoxy-psoralen; 5'-acetyl-4,8-dimethyl-psoralen; 5'-aceto-8-methyl-psoralen; and 5'-aceto-4,8-dimethyl-psoralen Exemplary purpurins include octaethylpurpurin; octaethylpurpurin zinc; oxidized octaethylpurpurin; reduced octaethylpurpurin; reduced octaethylpurpurin tin; purpurin 18; purpurin-18; purpurin-18-methyl ester; purpurin; tin ethyl etiopurpurin I; Zn(II)aetio-purpurin ethyl ester; and zinc etiopurpurin.

Exemplary quinones include 1-amino-4,5-dimethoxy anthraquinone; 1,5-diamino-4,8-dimethoxy anthraquinone;

1,8-diamino-4,5-dimethoxy anthraquinone; 2,5-diamino-1,8-dihydroxy anthraquinone; 2,7-diamino-1,8-dihydroxy anthraquinone; 4,5-diamino-1,8-dihydroxy anthraquinone; mono-methylated 4,5- or 2,7-diamino-1,8-dihydroxy anthraquinone; anthralin(keto form); anthralin; anthralin anion; 1,8-dihydroxy anthraquinone; 1,8-dihydroxy anthraquinone(Chrysazin); 1,2-dihydroxy anthraquinone; 1,2-dihydroxy anthraquinone(Alizarin); 1,4-dihydroxy anthraquinone(Quinizarin); 2,6-dihydroxy anthraquinone; 2,6-dihydroxy anthraquinone(Anthraflavin); 1-hydroxy anthraquinone(Erythroxy-anthraquinone); 2-hydroxy-anthraquinone; 1,2,5,8-tetra-hydroxy anthraquinone (Quinalizarin); 3-methyl-1,6,8-trihydroxy anthraquinone (Emodin); anthraquinone; anthraquinone-2-sulfonic acid; benzoquinone; tetramethyl benzoquinone; hydroquinone; chlorohydroquinone; resorcinol; and 4-chlororesorcinol.

Exemplary retinoids include all-trans retinal; $C_{17}$ aldehyde; $C_{22}$ aldehyde; 11-cis retinal; 13-cis retinal; retinal; and retinal palmitate.

Exemplary rhodamines include 4,5-dibromo-rhodamine methyl ester; 4,5-dibromo-rhodamine n-butyl ester; rhodamine 101 methyl ester; rhodamine 123; rhodamine 6G; rhodamine 6G hexyl ester; tetrabromo-rhodamine 123; and tetramethyl-rhodamine ethyl ester.

Exemplary thiophenes include terthiophenes such as 2,2':5',2"-terthiophene; 2,2':5',2"-terthiophene-5-carboxamide; 2,2':5',2"-terthiophene-5-carboxylic acid; 2,2':5',2"-terthiophene-5-L-serine ethyl ester; 2,2':5',2"-terthiophene-5-N-isopropynyl-formamide; 5-acetoxymethyl-2,2':5',2"-terthiophene; 5-benzyl-2,2':5',2"-terthiophe sulphide; 5-benzyl- 2,2':5',2"-terthiophene-sulfoxide; 5-benzyl-2,2':5',2"-terthiophene-sulphone; 5-bromo-2,2':5',2"-terthiophene; 5-(butynyl-3'''-hydroxy)-2,2':5',2"-terthiophene; 5-carboxyl-5"-trimethylsilyl-2,2':5',2"-terthiophene; 5-cyano-2,2':5',2"-terthiophene; 5,5"-dibromo-2,2':5',2"-terthiophene; 5-(1''',1'''-dibromoethenyl)-2,2':5',2'''-terthiophene; 5,5"-dicyano-2,2':5',2"-terthiophene; 5,5"-diformyl-2,2':5',2"-terthiophene; 5-difluoromethyl-2,2':5',2"-terthiophene; 5,5"-diiodo-2,2':5',2"-terthiophene; 3,3"-dimethyl-2,2':5',2"-terthiophene; 5,5"-dimethyl-2,2':5',2"-terthiophene; 5-(3''',3'''-dimethylacryloyloxymethyl)-2,2':5',2"-terthiophene; 5,5"-di-(t-butyl)-2,2':5',2"-terthiophene; 5,5"-dithiomethyl-2,2':5',2"-terthiophene; 3'-ethoxy 2,2':5',2"-terthiophene; ethyl 2,2':5',2"-terthiophene-5-carboxylic acid; 5-formyl-2,2':5',2"-terthiophene; 5-hydroxyethyl-2,2':5',2"-terthiophene; 5-hydroxymethyl-2,2':5',2"-terthiophene; 5-iodo-2,2':5',2"-terthiophene; 5-methoxy-2,2':5',2"-terthiophene; 3'-methoxy-2,2':5',2"-terthiophene; 5-methyl-2,2':5',2"-terthiophene; 5-(3'''-methyl-2'''-butenyl)-2,2':5',2"-terthiophene; methyl 2,2':5',2"-terthiophene-5-[3'''-acrylate]; methyl 2,2':5',2"-terthiophene-5-(3'''-propionate); N-allyl-2,2':5',2"-terthiophene-5-sulphonamide; N-benzyl-2,2':5',2"-terthiophene-5-sulphonamide; N-butyl-2,2':5',2"-terthiophene-5-sulphonamide; N,N-diethyl-2,2':5',2"-terthiophene-5-sulphonamide; 3,3',4',3"-tetramethyl-2,2':5',2"-terthiophene; 5-t-butyl-5"-trimethylsilyl-2,2':5',2"-terthiophene; 3'-thiomethyl-2,2':5',2"-terthiophene; 5-thiomethyl-2,2':5',2"-terthiophene; 5-trimethylsilyl-2,2':5',2"-terthiophene, bithiophenes such as 2,2'-bithiophene; 5-cyano-2,2'-bithiophene; 5-formyl-2,2'-bithiophene; 5-phenyl-2,2'-bithiophene; 5-(propynyl)-2,2'-bithiophene; 5-(hexynyl)-2,2'-bithiophene; 5-(octynyl)-2,2'-bithiophene; 5-(butynyl-4"-hydroxy)-2,2'-bithiophene; 5-(pentynyl-5"-hydroxy)-2,2'-bithiophene; 5-(3",4"-dihydroxybutynyl)-2,2'-bithiophene derivative; 5-(ethoxybutynyl)-2,2'-bithiophene derivative, and misclaneous thiophenes such as 2,5-diphenylthiophene; 2,5-di(2-thienyl)furan; pyridine,2,6-bis(2-thienyl)-; pyridine, 2,6-bis(thienyl)-; thiophene, 2-(1-naphthalenyl)-; thiophene, 2-(2-naphthalenyl)-; thiophene, 2,2'-(1,2-phenylene)bis-; thiophene, 2,2'-(1,3-phenylene) bis-; thiophene, 2,2'-(1,4-phenylene)bis-; 2,2':5',2":5"',2"''-quaterthiophene; α-quaterthienyl; α-tetrathiophene; α-pentathiophene; α-hexathiophene; and α-heptathiophene.

Exemplary verdins include copro(II)verdin trimethyl ester; deuteroverdin methyl ester; mesoverdin methyl ester; and zinc methyl pyroverdin.

Exemplary vitamins include ergosterol(provitamin D2); hexamethyl-Co a Co b-dicyano-7-de(carboxymethyl)-7,8-didehydro-cobyrinate(Pyrocobester); pyrocobester; and vitamin D3.

Exemplary xanthene dyes include Eosin B (4',5'-dibromo, 2',7'-dinitro-fluorescein, dianion); eosin Y; eosin Y (2',4',5',7'-tetrabromo-fluorescein, dianion); eosin(2',4',5',7'-tetrabromo-fluorescein, dianion); eosin(2',4',5',7'-tetrabromo-fluorescein, dianion) methyl ester; eosin(2',4',5',7'-tetrabromo-fluorescein, monoanion)p-isopropylbenzyl ester; eosin derivative(2',7'-dibromo-fluorescein, dianion); eosin derivative(4',5'-dibromo-fluorescein, dianion); eosin derivative(2',7'-dichloro-fluorescein, dianion); eosin derivative(4',5'-dichloro-fluorescein, dianion); eosin derivative(2',7'-diiodo-fluorescein, dianion); eosin derivative(4',5'-diiodo-fluorescein, dianion); eosin derivative (tribromo-fluorescein, dianion); eosin derivative(2',4',5',7'-tetrachloro-fluorescein, dianion); eosin; eosin dicetylpyridinium chloride ion pair; erythrosin B (2',4',5',7'-tetraiodo-fluorescein, dianion); erythrosin; erythrosin dianion; erythrosin B; fluorescein; fluorescein dianion; phloxin B (2',4',5',7'-tetrabromo-3,4,5,6-tetrachloro-fluorescein, dianion); phloxin B (tetrachloro-tetrabromo-fluorescein); phioxine B; rose bengal (3,4,5,6-tetrachloro-2',4',5',7'-tetraiodofluorescein, dianion); rose bengal; rose bengal dianion; rose bengal O-methyl-methylester; rose bengal 6'-O-acetyl ethyl ester; rose bengal benzyl ester diphenyl-duiodonium salt; rose bengal benzyl ester triethyl-lammonium salt; rose bengal benzyl ester, 2,4,6,-triphenylpyrilium salt; rose bengal benzyl ester, benzyltriphenyl-phosphonium salt; rose bengal benzyl ester, benzyltriphenyl phosphonium salt; rose bengal benzyl ester, diphenyl-iodonium salt; rose bengal benzyl ester, diphenyl-methylsulfonium salt; rose bengal benzyl ester, diphenyl-methyl-sulfonium salt; rose bengal benzyl ester, triethyl-ammonium salt; rose bengal benzyl ester, triphenyl pyrilium; rose bengal bis(triethyl-ammonium)salt)(3,4,5,6-tetrachloro-2',4',5',7'-tetraiodofluorescein, bis(triethyl-ammonium salt); rose bengal bis(triethyl-ammonium)salt; rose bengal bis(benzyl-triphenyl-phosphonium) salt(3,4,5,6-tetrachloro-2',4',5',7'-tetraiodofluorescein, bis(benzyl-triphenyl-phosphonium) salt); rose bengal bis(diphenyl-iodonium)salt(3,4,5,6-tetrachloro-2',4',5',7'-tetraiodofluorescein, bis(diphenyl-iodonium)salt); rose bengal di-cetyl-pyridinium chloride ion pair; rose bengal ethyl ester triethyl ammonium salt; rose bengal ethyl ester triethyl ammonium salt; rose bengal ethyl ester; rose bengal methyl ester; rose bengal octyl ester tri-n-butyl-ammonium salt RB; rose bengal, 6'-O-acetyl-, and ethyl ester.

Particularly preferred PSs are the green porphyrins, such as BPD-DA, -DB, -MA, and -MB, and in particular BPD-MA, EA6, and B3. These compounds are porphyrin derivatives obtained by reacting a porphyrin nucleus with an alkyne in a Diels-Alder type reaction to obtain a mondhydrobenzoporphyrin, and they are described in detail in the issued U.S. Pat. No. 5,171,749, which is hereby incorporated in its entirety by reference. Of course, combinations of photosensitizers may also be used. It is preferred that the absorption spectrum of the photosensitizer be in the visible range, typically between 350 nm and 1200 nm, more preferably between 400–900 nm, and even more preferably between 600–900 nm.

BPD-MA is described, for example, in U.S. Pat. No. 5,171,749; EA6 and B3 are described in U.S. Ser. Nos. 09/088,524 and 08/918,840, respectively, all of which are incorporated herein by reference. Preferred green porphyrins have the basic structure:

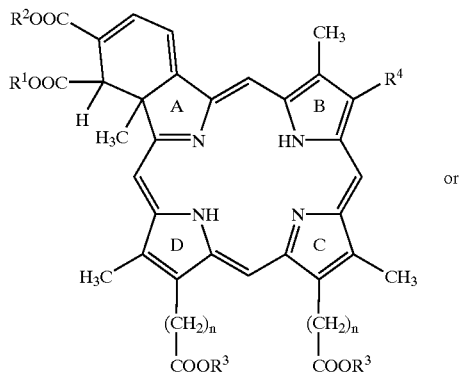

1 or

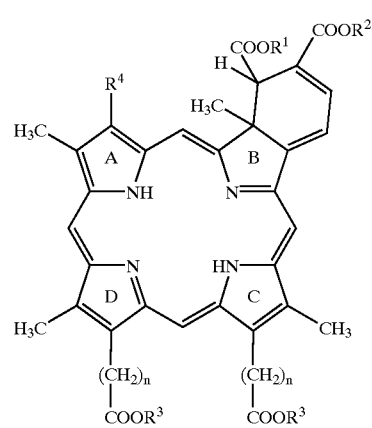

2 or

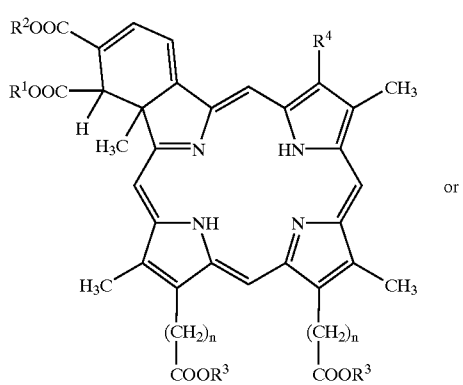

3

-continued

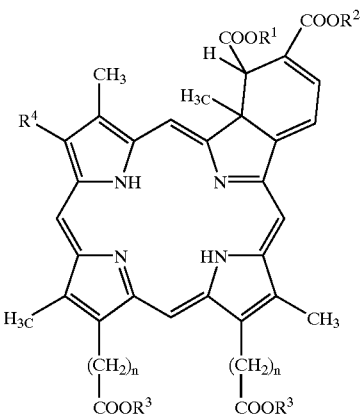

4 where $R^4$ is vinyl or 1-hydroxyethyl and $R^1$, $R^2$, and $R^3$ are H or alkyl or substituted alkyl.

BPD-MA has the structure shown in formula 1 wherein $R^1$ and $R^2$ are methyl, $R^4$ is vinyl and one of $R^3$ is H and the other is methyl. EA6 is of formula 2 wherein $R^1$ and $R^2$ are methyl and both $R^3$ are 2-hydroxyethyl (i.e., the ethylene glycol esters). B3 is of formula 2 wherein $R^1$ is methyl, $R^2$ is H, and both $R^3$ are methyl. In both EA6 and B3, $R^4$ is also vinyl.

The representations of BPD-MA$_C$ and BPD-MA$_D$, which are the components of Verteporfin™, as well as illustrations of A and B ring forms of EA6 and B3, are as follows:

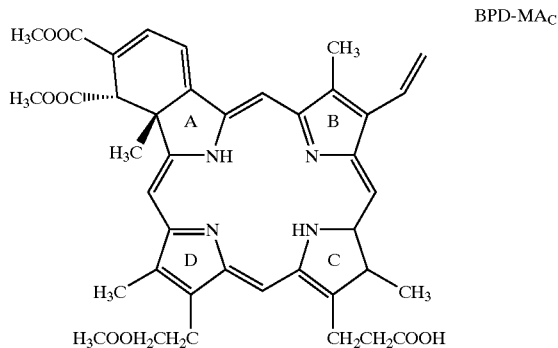

BPD-MA$_C$

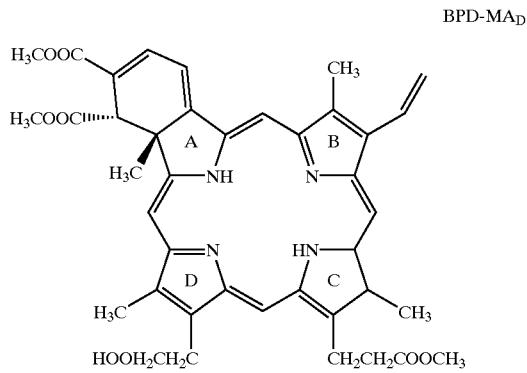

BPD-MA$_D$

-continued

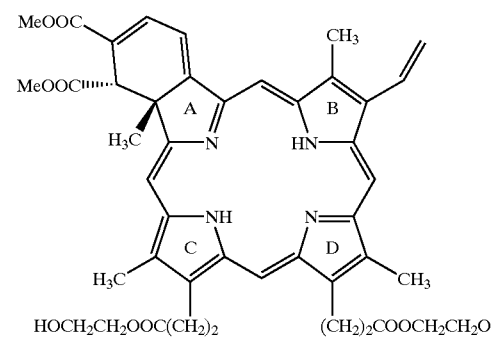
A-EA6

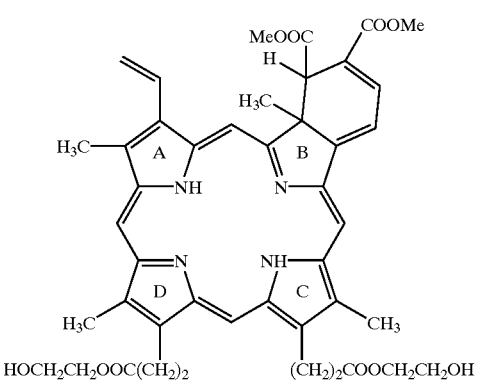
B-EA6

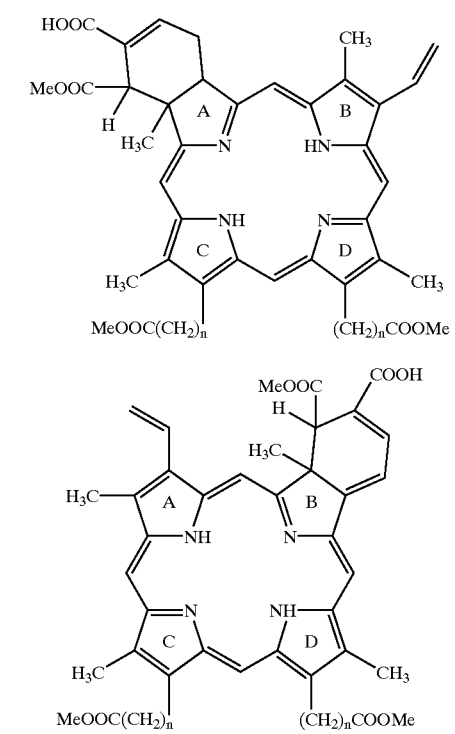
A-B3

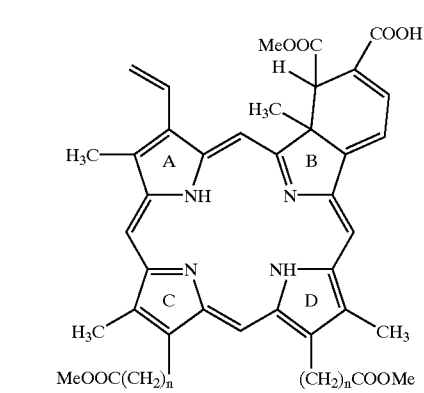
B-B3

Related compounds of formulas 3 and 4 are also useful; in general, $R^4$ will be vinyl or 1-hydroxyethyl and $R^1$, $R^2$, and $R^3$ are H or alkyl or substituted alkyl.

As indicated above, attaining a low-dose PDT protocol depends on the balance of the concentration of PS employed, light intensity, and time of irradiation which determines total energy. The values set forth hereinbelow for these parameters indicates the range in which they may be varied; however, the upper ranges of one parameter may mandate lower ranges of another.

The PS concentration in the formulation to be administered will depend on the nature of the target vein graft to be treated, the manner in which the formulation is contacted with the graft, and the nature of the PS. Typical concentrations, however, are in the range of about 1 ng/ml to about 10 μg/ml, preferably about 2 ng/ml to about 1 μ/ml, and typically in the range of about 10 ng/ml to about 100 ng/ml. However, these values are merely suggestions and may not apply to all PSs. For localized application of BPD-MA and other green porphyrins or porphyrin derivatives (especially those listed above), a range of about 0.01 to about 0.2 or about 0.5 mg/ml is contemplated. Preferably, about 0.075 mg/ml is used. For systemic application of PS, the range should be lower than that used for treating neovasculature, which is about 2–8 (or more preferably 6) mg/m$^2$ (BPD-MA/body surface area). Preferably, a range of less than about 0.1–2 mg/m$^2$ of BPD-MA is used.

As an additional example, and without limiting the invention, Photofrin™ may be administered locally at a concentration of about 0.01 to about 10 mg/ml, preferably at about 2.5 mg/ml. These concentrations may also be used with other green porphyrins or porphyrin derivatives (especially those listed above).

Systemic administration can also be stated in terms of amount of PS to body weight of the subject being treated. Dosages for this invention stated in such terms are less than about 10 μg/kg to 100 mg/kg body weight, preferably less than 100 μg/kg to 10 mg/kg, more preferably less than about 1 mg/kg in mice and less than about 0.2 mg/kg in humans. Optimizing the concentration of a particular photosensitizer within a therapeutically active range is well within the skill in the art and routinely practiced. Systemic administration of Photofrin™ may be via introduction of about 0.15 mg/kg of the subject's body weight.

The additional components in the formulation used to treat the target vein graft are also dependent on the nature of the PS and the nature of the material to be treated. The formulation may be a liposomal formulation, an emulsion, or simply an aqueous solution. Buffers and other excipients may also be added. Gelling agents and other excipients may also be employed.

The time of treatment with photosensitizer is also variable depending on the nature of the components of the system, but typically an incubation time of less than 5 minutes-1 hour before irradiation is used in the invention. Preferably, the incubation time is between 1 minute and 1 hour. The incubation may occur in the dark and subsequent radiation supplied, or low-level light may be supplied during PS administration.

Following PS administration, treatment with radiation absorbed by the PS may be performed by any means, including transcutaneous irradiation of a large area. The irradiation levels will be in the range generally employed for low-light-dose photodynamic therapy as described hereinabove. These typical levels are in the range of less than 25 J/cm$^2$, preferably less than 10 J/cm$^2$, more preferably less than 2 J/cm$^2$ or less than 1 J/cm$^2$. The radiation can be supplied by any convenient source using a wavelength absorbed by the PS used. Examples of sources for use in the present methods include any assembly capable of producing visible light.

A preferred method of performing the invention is by using extralumenal irradiation. While this may be accomplished with any suitable light source, the use of a diffuser wrapped around the blood vessel or anastomosis is preferred.

One surprising aspect of the invention is that PDT with low doses (0.15 mg/2 ml) of locally delivered BPD-MA followed by irradiation with ambient light from operating room lamps resulted in the reduction of IH at the anastomosis of the arteriovenous grafts. Unexpectedly, PDT with high doses of BPD-MA either did not modulate the development of IH or actually induced IH.

As such, low-dose PDT is a preferred embodiment of the invention which produces a marked difference in IH in the vein of AV fistulae after one and three months. Forty-eight hours after fistula creation low-dose PDT decreased the number of actively dividing cells in the media of the treated veins, without significantly affecting SMC number. Low-dose PDT does not appear to disturb the endothelial lining or the elastic lamina of the vessel wall. Also, low-dose PDT did not significantly affect the medial thickening of veins that is associated with normal maturation of arteriovenous fistulae. Thus low-dose PDT safely and effectively inhibits the onset of IH at the anastomosis of AV fistulae.

The following examples are intended to illustrate but not to limit the invention.

EXAMPLE 1

Materials and Methods Used

Domestic swine (male, 40–50 kg) were used for experiments related to the present invention. Extensive research has been performed to characterize the changes leading to intimal hyperplasia (IH) in the arteries and veins of swine, which closely resemble those in humans (22). AV fistulae were created in several pigs to confirm that measurable IH developed in the vein, just distal to the anastomoses, within one month (FIG. 1A).

Figure 1B:
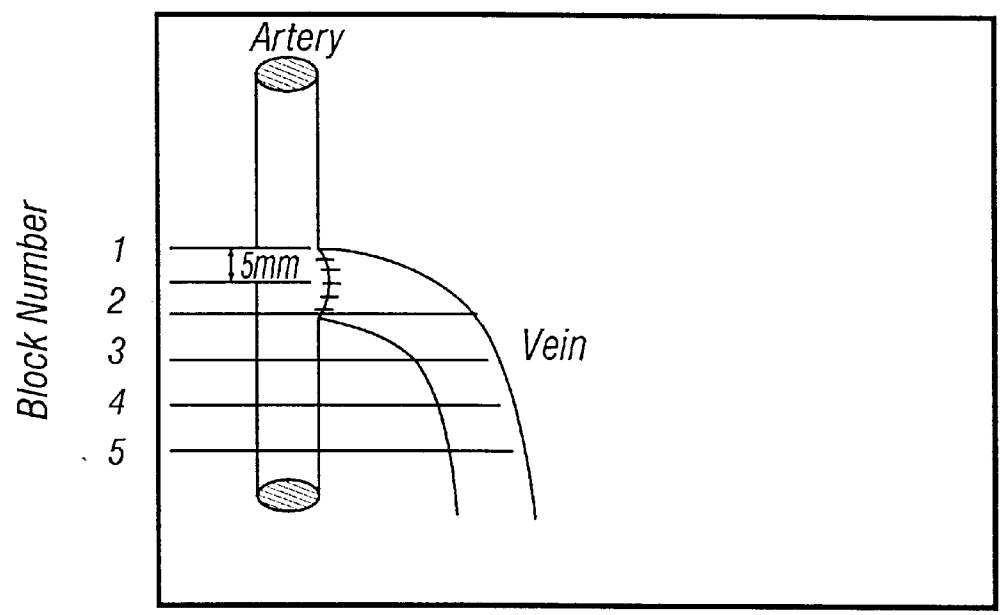
FIG. 1B is a schematic of an AV fistula in cross-section. Horizontal lines indicate orientation of excised tissue as blocks to be embedded for histological and immunocytochemical analysis.
Figure 2:
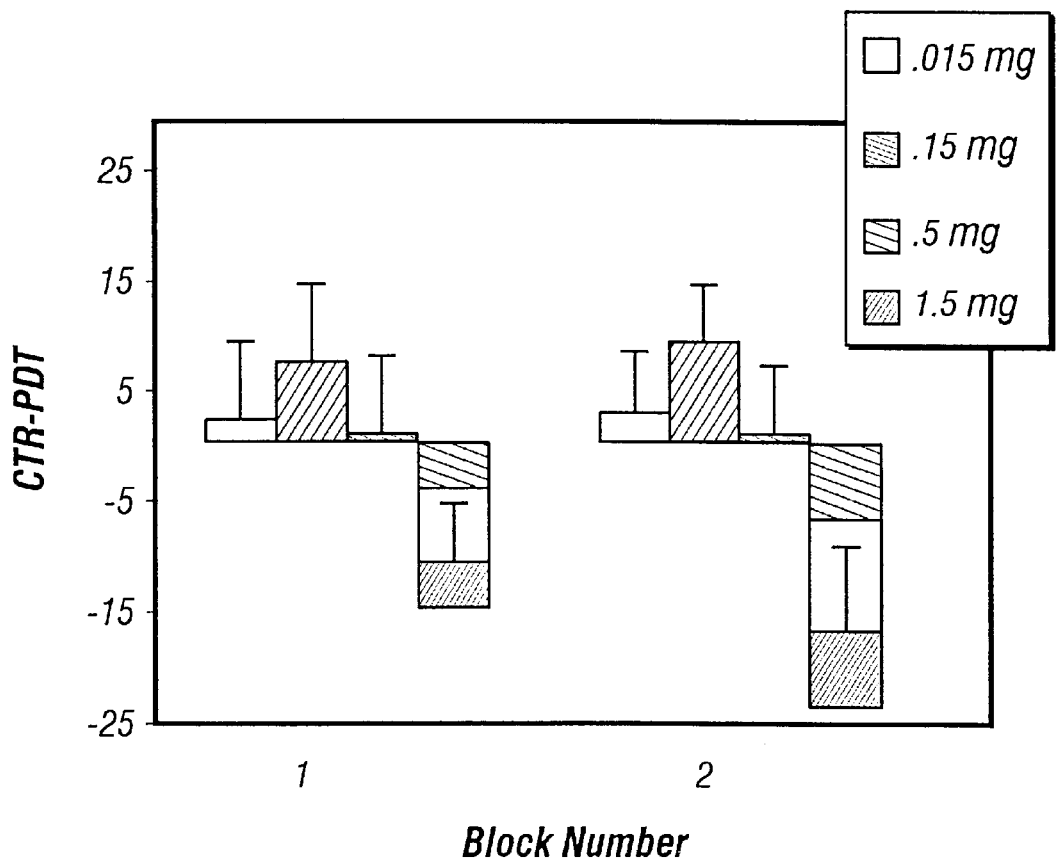
FIG. 2 shows the difference in the percent of the lumen area compromised by intimal hyperplasia between control and PDT-treated fistulae after one month (operating room lamp only).

Pigs were recovered and left for four weeks at which time they were exsanguinated and perfused with 10% formalin. The fistulae were surgically excised for processing and wax embedding for histology (FIGS. 1A and 2). Wax blocks containing the fistulae were cut to provide sections containing a cross-section of the anastomoses, including the artery and vein distal to the sutures (FIGS. 1A, 1B, and 3).

A porous balloon catheter was introduced into the lumen of veins to deliver either 2 mL of BPD-MA (diluted in 5% dextrose in water) or 5% dextrose in water (control), at a delivery pressure of 2 mm Hg. Two minutes later, the photosensitizer (or dextrose) was rinsed out with heparinized saline before light exposure.

The adventitia of the vein was exposed to the operating room (OR) lamp light for 40 minutes (a combination of incandescent bulbs and fluorescence tubes—approximately 1 J/cm$^2$).

Measurements and observations were made by morphometric analysis of cross-sections of fistulae stained with Verhoeff's elastic to assess the integrity of the vessel wall and also clearly demarcate the internal elastic lamina (IEL) for the measurement of IH. Areas within the lumen and those circumscribed by the internal elastic lamina (IEL) and the external elastic lamina (EEL) were measured directly using the Optimas (Optimas Corporation, Bothell, Wash., USA) program. The areas of the intima and the media were calculated by subtraction: intimal area equals the EEL area minus the lumen area, and medial area equals EEL area minus IEL area.

In Example 4, immunohistochemistry was use to study the early phase of cell proliferation. Immunocytochemistry for the proliferating cell nuclear antigen (PCNA, mouse antibody clone PC10, Sigma) was used to assess cell proliferation in the vein. PCNA positive cells were counted using the Optimas image analysis program.

In Example 4, the cell content of the vein wall was also examined using immunohistochemical techniques to detect SMCs (mouse anti-human ax-smooth muscle actin, clone 1A4 (Dako, Mississauga, Canada)), macrophages (mouse monoclonal anti-human monocyte/macrophage, clone MAC 387 (Serotec Inc.), T cells (Rabbit anti-human CD3 with Neo marker), and endothelial cells (rabbit polyclonal anti-human von Willebrand Factor (Dako, Mississauga, Canada)). SMCs were counted using the Optimas image analysis program and macrophages were counted manually using Image Pro Plus 3 (Media Cybernetics, Silver Spring, Md., USA).

Statistical analysis was conducted using the two tailed t-Test (two-sample assuming unequal variances) for comparisons between groups of PDT-treated and control fistulae and paired t-tests for paired comparisons of PDT-treated and control fistulae.

EXAMPLE 2

Optimization of Drug and Radiation Dose

End-to-side AV fistulae between the carotid artery and internal jugular vein were treated at four different BPD-MA doses (0.015, 0.15, 0.5 & 1.5 mg/2 mL) and exposed to 40 minutes of operating room (OR) lamp and ambient light to determine the optimal doses required to inhibit IH while causing minimal damage to the vein wall. Bilateral AV fistulae were created. For example, one side was treated with saline and 40 min. OR lamp light, while the other side was treated with BPD-MA (0.015 mg/2 mL or the other doses) and 40 min. OR lamp light after creating the anastomoses. At least six pigs were treated using each BPD-MA dose and the 40 minutes OR lamp light delivery system.

Optimization of PS and radiation dose was performed. Bilateral end-to-side AV fistula between the carotid artery and jugular vein were created in 29 pigs. Animals were sacrificed 4 weeks after PDT, and the fistulae were surgically excised and processed for histology. Computer-assisted measurement of the lumen area and,the area delimited by the internal elastic lamina (IEL) and external elastic lamina (EEL) was performed on 5 sections of the vein. The IH was calculated by subtracting the lumen area from the EEL area. Medial hyperplasia was calculated by subtracting the IEL area from the EEL area.

For each fistula, the percent of the lumen compromised by the intima hyperplasia (%LCIH=IEL−Lumen/IEL) was calculated for the first two complete blocks from the tip of the anastomosis, since IH is most often observed clinically within 1 cm of the anastomosis. Differences in the % LCIH between control and treated sides were averaged for each dose group. Results are presented in Tables 1 a and 1b as well as illustrated in FIGS. 2 and 3.

TABLE 1a

Percent of lumen area compromised by intimal hyperplasia (one month)
0.015 mg BPD-MA
Percent Lumen Compromised by Intimal Hyperplasia

| | PDT | | Control | | Control-PDT | |
| --- | --- | --- | --- | --- | --- | --- |
| Pig # | Block #1 | Block #2 | Block #1 | Block #2 | Block #1 | Block #2 |
| OR Lamp | | | | | | |
| 1 | 3.1 | 2.4 | 2.9 | 2.2 | −0.2 | −0.2 |
| 2 | 21.3 | 2.3 | 31.5 | 29.4 | 10.2 | 27.1 |
| 3 | 9 | 5 | 5 | 3 | −4 | −2 |
| 4 | 30.3 | 13 | 3.1 | 6.5 | −27.2 | −6.5 |
| 5 | 3.4 | 8.6 | 28.3 | 6.7 | 24.9 | −1.9 |
| 6 | T | T | 29.5 | 9.9 | | |
| 7 | 2.2 | 1.8 | 7.5 | 2.7 | 5.3 | 0.9 |

TABLE 1a-continued

| | | | | | |
|---|---|---|---|---|---|
| Mean | 11.6 | 5.5 | 15.4 | 8.6 | 1.5 | 2.9 |
| STD | 11.6 | 4.5 | 13.6 | 9.6 | 17.3 | 12.1 |
| SEM | 5.2 | 2.0 | 5.5 | 3.9 | 7.7 | 5.4 |

Block 1 p = 0.39    Block 2 p = 0.36*
*two tailed Student's t test between PDT-treated and control samples for each block 0.15 mg BPD-MA
Percent Lumen Compromised by Intimal Hyperplasia

| | PDT | | Control | | Control-PDT | |
|---|---|---|---|---|---|---|
| Pig # | Block# 1 | Block# 2 | Block# 1 | Block# 2 | Block# 1 | Block# 2 |
| OR Lamp | | | | | | |
| 1 | T | T | 23.5 | 8.2 | | |
| 2 | 7.1 | 7 | 31.2 | 9.7 | 24.2 | 2.7 |
| 3 | 19.3 | 9.1 | T | T | | |
| 4 | 4.6 | 6.7 | 3.1 | 21.5 | −1.5 | 14.8 |
| 5 | 9.2 | 2.5 | 17.4 | 3 | 8.2 | 0.5 |
| 6 | 6.9 | 3.6 | T | T | | |
| 7 | 21.1 | 8.6 | 18.2 | 27.6 | −2.9 | 19 |
| Mean | 11.4 | 6.3 | 18.7 | 14.0 | 7.0 | 9.25 |
| STD | 7.0 | 2.7 | 10.3 | 10.2 | 12.5 | 9.0 |
| SEM | 3.1 | 1.2 | 5.2 | 5.1 | 7.2 | 5.2 |

Block 1 p = 0.095    Block 2 p = 0.06*
*two tailed Student's t test between PDT-treated and control samples for each block 0.5 mg BPD-MA
Percent Lumen Compromised by Intimal Hyperplasia

| | PDT | | Control | | Control-PDT | |
|---|---|---|---|---|---|---|
| Pig # | Block# 1 | Block# 2 | Block# 1 | Block# 2 | Block# 1 | Block# 2 |
| OR Lamp | | | | | | |
| 1 | T | T | 19.5 | 3.0 | | |
| 2 | 18.1 | 11.2 | 5.1 | 2.9 | −13.0 | −8.3 |
| 3 | 16.6 | 6.8 | 21.7 | 8.9 | 5.1 | 2.1 |
| 4 | 32.0 | 3.4 | 41.4 | 12.4 | 9.4 | 9.0 |
| 5 | T | T | T | T | | |
| Mean | 22.2 | 7.1 | .21.9 | 6.8 | 0.5 | 0.9 |
| STD | 8.5 | 3.9 | 14.9 | 4.7 | 11.9 | 8.7 |
| SEM | 6.0 | 2.8 | 8.6 | 2.7 | 8.4 | 6.2 |

1.5 mg BPD-MA
Percent Lumen Compromised by Intimal Hyperplasia

| | PDT | | Control | | Control-PDT | |
|---|---|---|---|---|---|---|
| Pig # | Block# 1 | Block# 2 | | Block# 2 | Block# 1 | Block# 2 |
| OR lamp | | | | | | |
| 1 | 19.4 | 43.0 | 18.7 | 5.1 | −0.7 | −37.9 |
| 2 | 17.4 | 1.7 | 3.7 | 6.8 | −13.7 | 5.1 |
| 3 | 21.6 | 11.7 | T | T | | |
| 4 | 41.8 | 53.8 | 2.9 | 3.9 | −38.9 | −49.9 |
| 5 | 12.7 | 13.9 | 6.5 | 2.1 | −6.2 | −11.8 |
| 6 | T | T | T | T | | |

TABLE 1a-continued

| | | | | | |
|---|---|---|---|---|---|
| Mean | 22.6 | 24.8 | 8.0 | 4.5 | −14.9 | −23.6 |
| STD | 11.2 | 22.3 | 7.3 | 2.0 | 16.9 | 24.9 |
| SEM | 5.6 | 11.2 | 4.2 | 1.1 | 9.7 | 14.4 |

T = thrombosed

TABLE 1b

Percent Medial Hyperplasia (One month Data)
0.15 mg BPD-MA

| | Medial Hyperplasia | | | |
|---|---|---|---|---|
| | PDT | | Control | |
| Pig # | Block# 1 | Block# 2 | Block# 1 | Block# 2 |
| OR Lamp | | | | |
| 1 | T | T | 36.4 | 15.9 |
| 2 | 5.9 | 10.3 | 17.9 | 11.0 |
| 3 | 15.3 | 5.7 | T | T |
| 4 | 6.2 | 18.2 | 3.8 | 5.2 |
| 5 | 12.5 | 9.8 | 12.4 | 18.0 |
| 6 | 9.8 | 13.7 | T | T |
| Mean | 10.0 | 11.5 | 17.6 | 12.5 |
| STD | 4.1 | 4.7 | 13.8 | 5.7 |
| SEM | 2.0 | 2.3 | 8.0 | 3.3 |

Whereas little change was noticed in the amount of IH between control veins and those treated with the dose of 0.015 mg BPD-MA, a 7.0% and 9.3% reduction in % LCIH was observed in the first and second blocks of the fistulae treated with 0.15 mg BPD-MA. Little difference between the treated and control fistulae was observed with 0.5 mg BPD-MA and treatment with the 1.5 mg dose appeared to induce IH (FIG. 2).

Figure 3A:
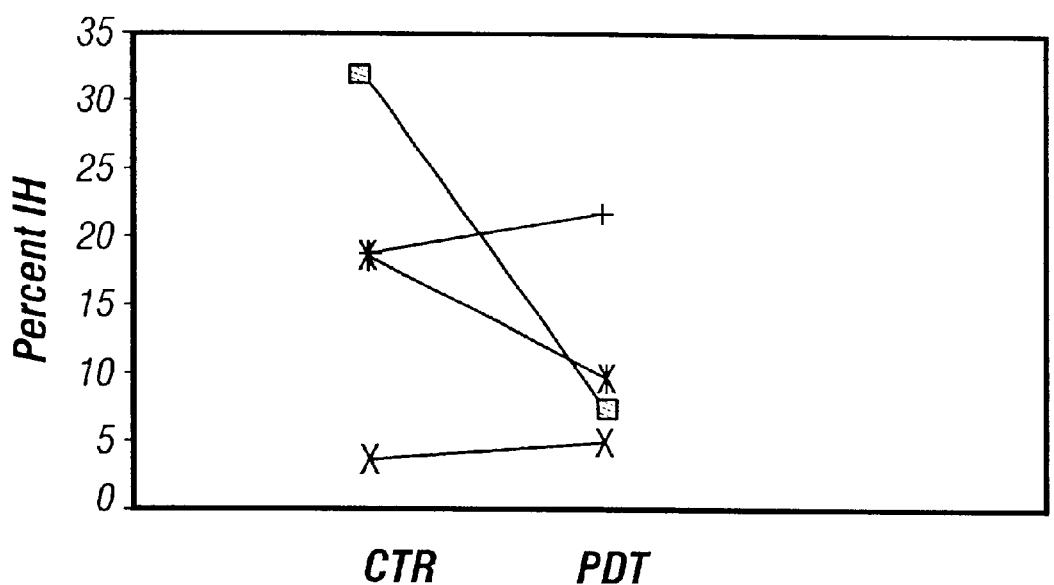
FIGS. 3A and 3B show paired data, from Block 1 and Block 2, respectively, illustrating the change in percent IH with PDT treatment within each of four animals.
Figure 3B:
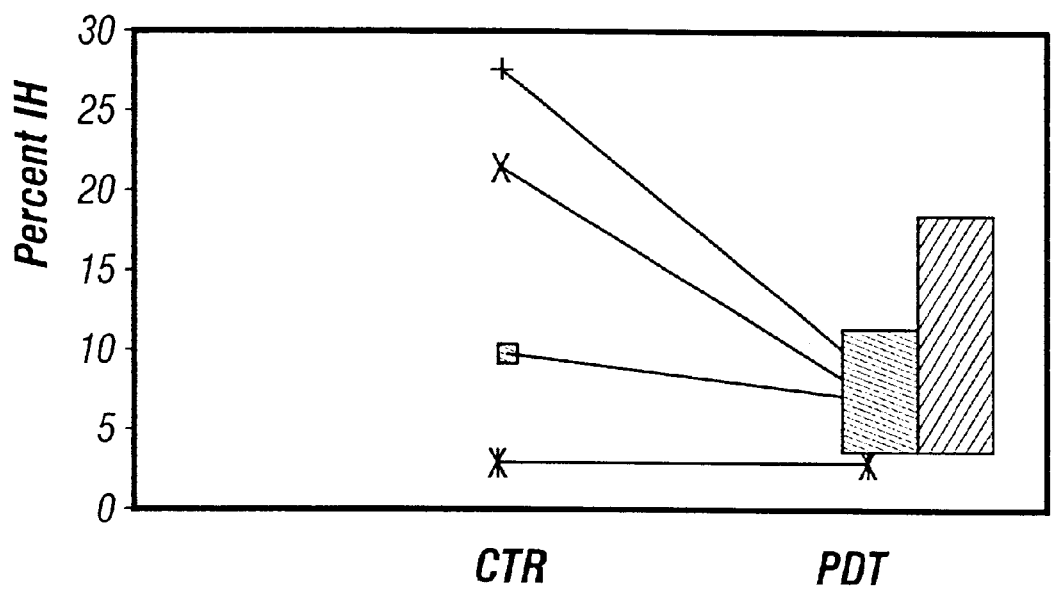
Figure 3C:
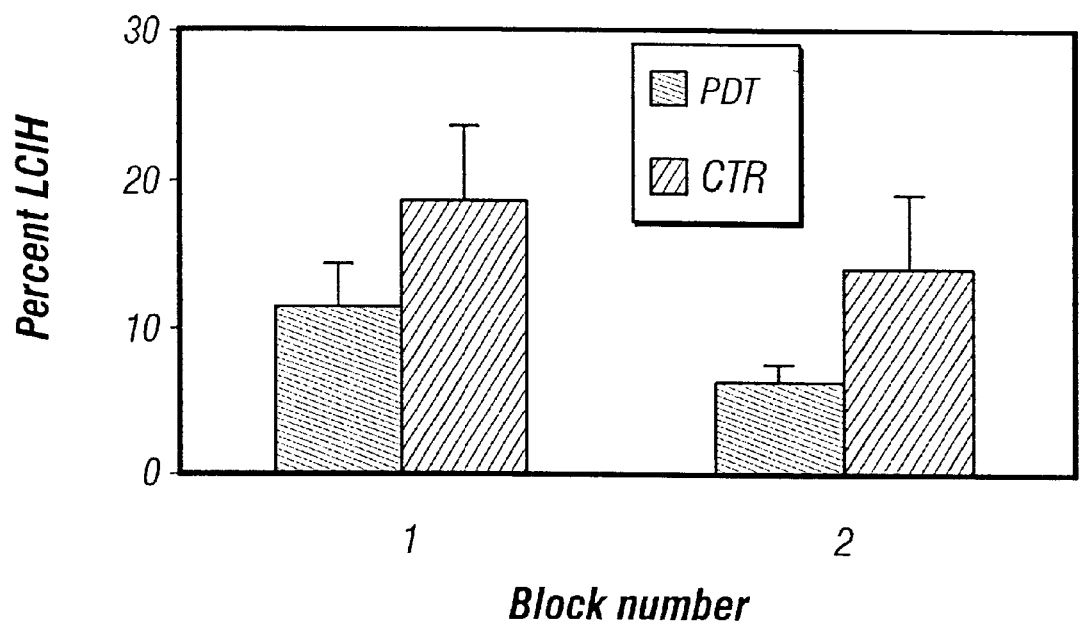
FIG. 3C shows the mean percent intimal hyperplasia compromising the lumen in PDT-treated (0.15 mg/2 mL) blocks compared to control blocks after one month (n=7).

The average % LCIH in the control group for 0.15 mg BPD-MA was 18.7% and 14% the first and second blocks, respectively (Table 1a). FIGS. 3A and 3B show the individual changes that were observed, in Block 1 and Block 2, respectively, between the PDT-treated and CTR fistulae in animals treated with 0.15 mg of BPD-MA (Verteporfin™). The mean PDT-induced decrease in intimal hyperplasia translated into a relative reduction of 38% and 55% respectively (FIG. 3C). The group mean data does not preserve the relationship between the PDT treated and control fistulae within the same animal.

Figure 3D:
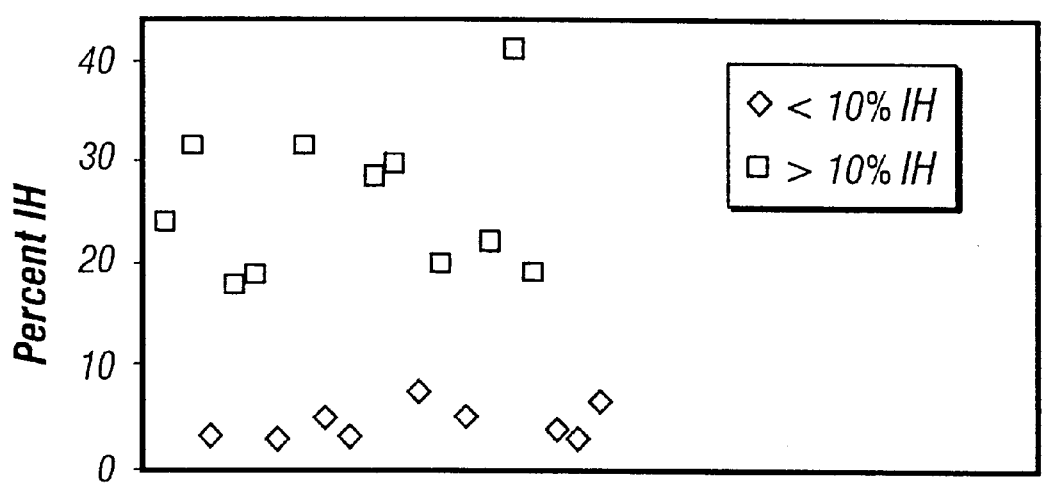
FIGS. 3D and 3E show scattergrams of IH in control veins; the percent 1H was measured in the vein of control fistulae in Block 1 (FIG. 3D) and Block 2 (FIG. 3E).
Figure 3E:
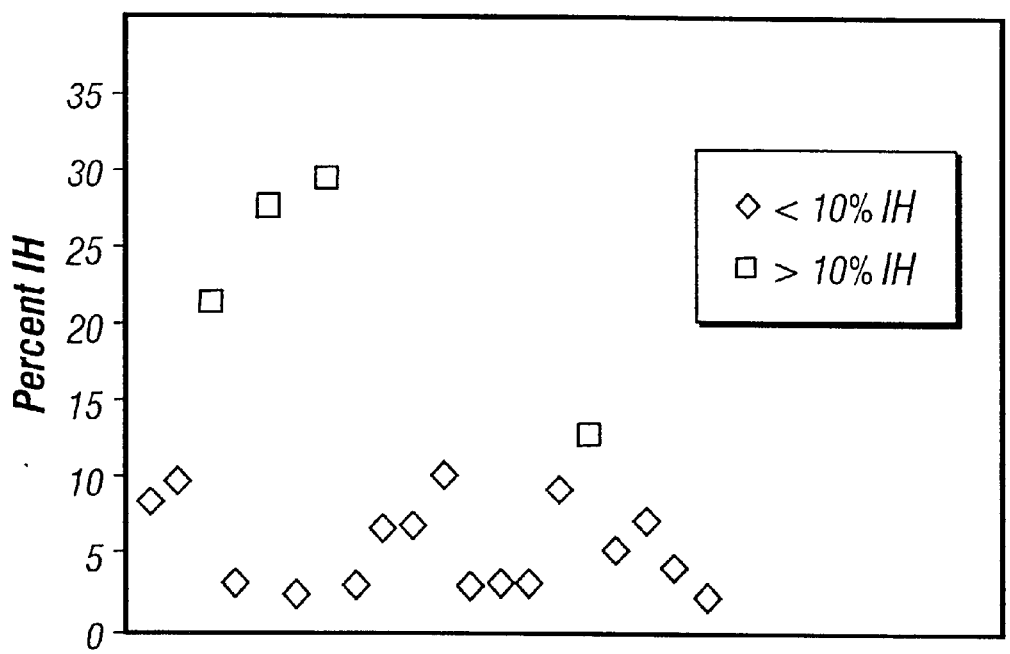

The paired data show that the biggest response to PDT was observed in animals that had a higher percentage of the vein occluded by IH in the control fistula. Scattergrams of the percent IH in the veins of control fistulae suggest that there were two populations of pigs with respect to the tendency to develop IH (FIGS. 3D and 3E).

Figure 3F:
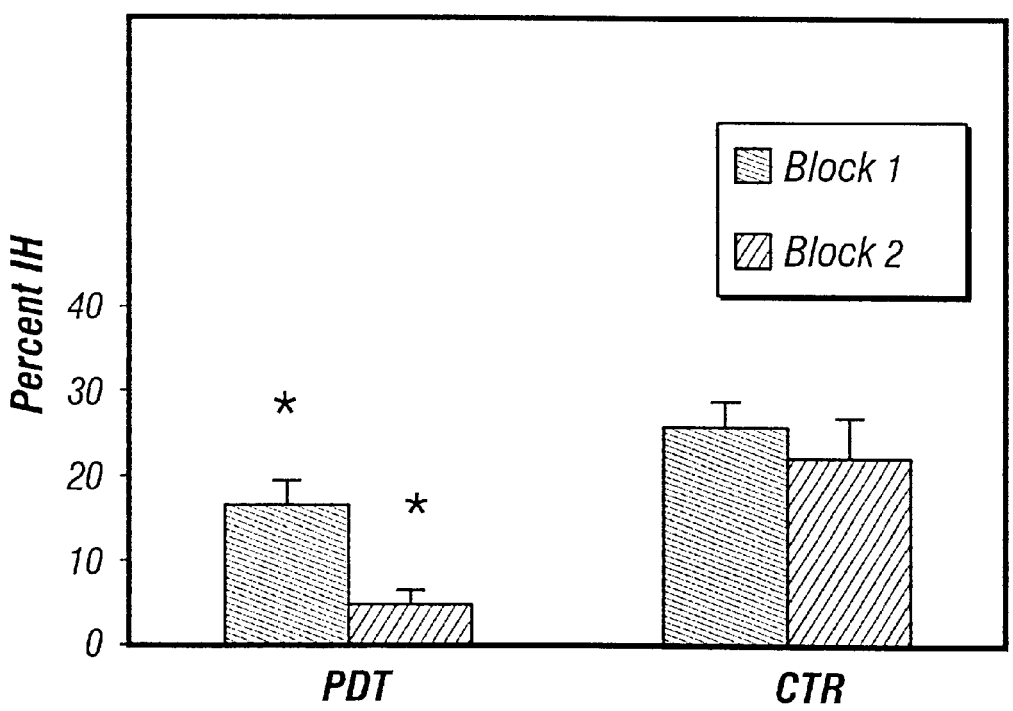
FIG. 3F shows the mean percent IH in all animals (0.015 mg to 1.5 mg/ml BPD-MA) with 10% IH or greater in Block 1 (n=8) and Block 2 (n=4) of control veins.

If all animals treated (0.015 to 1.5 mg/2 ml BPD-MA) are considered, and all animals which developed less than 10% IH in the control fistulae are considered non-responders and therefore excluded, the mean percent IH for blocks 1 and 2 would appear as shown in FIG. 3F. The percent IH in the PDT-treated fistulae was significantly less than that of the control fistulae in both Block 1 (p=0.03) and Block 2 (p=0.02).

Figure 4:
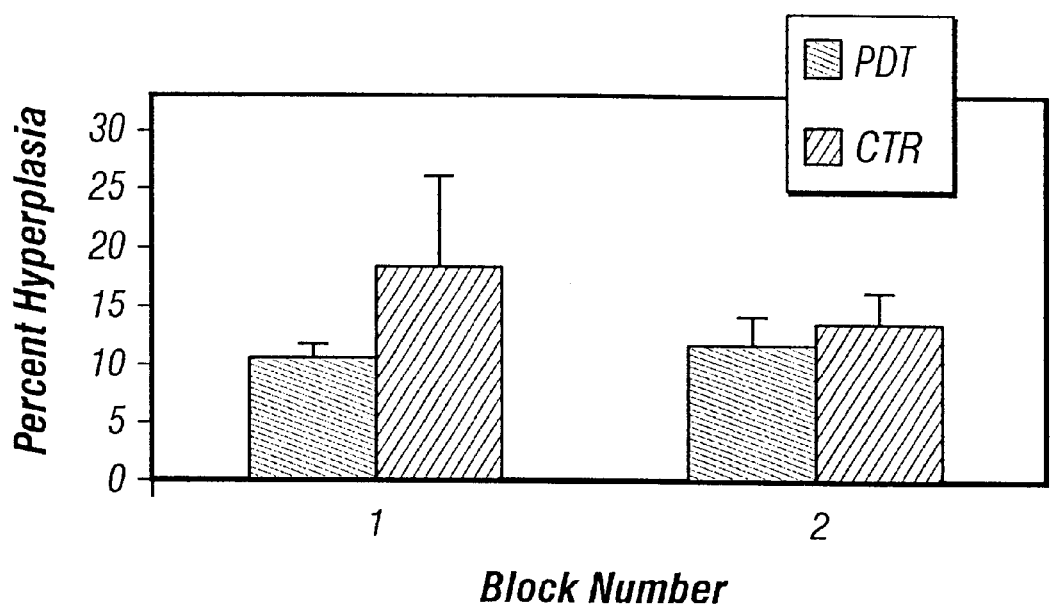
FIG. 4 shows the mean percent medial hyperplasia in PDT-treated (0.15 mg/2 mL) blocks compared to control blocks after one month (n=7).

Also, a 44% difference in medial thickness between the PDT-treated (0.15 mg/2 mL) and control samples was observed in the first block but little difference was observed in block 2 (FIG. 4).

Figure 5:
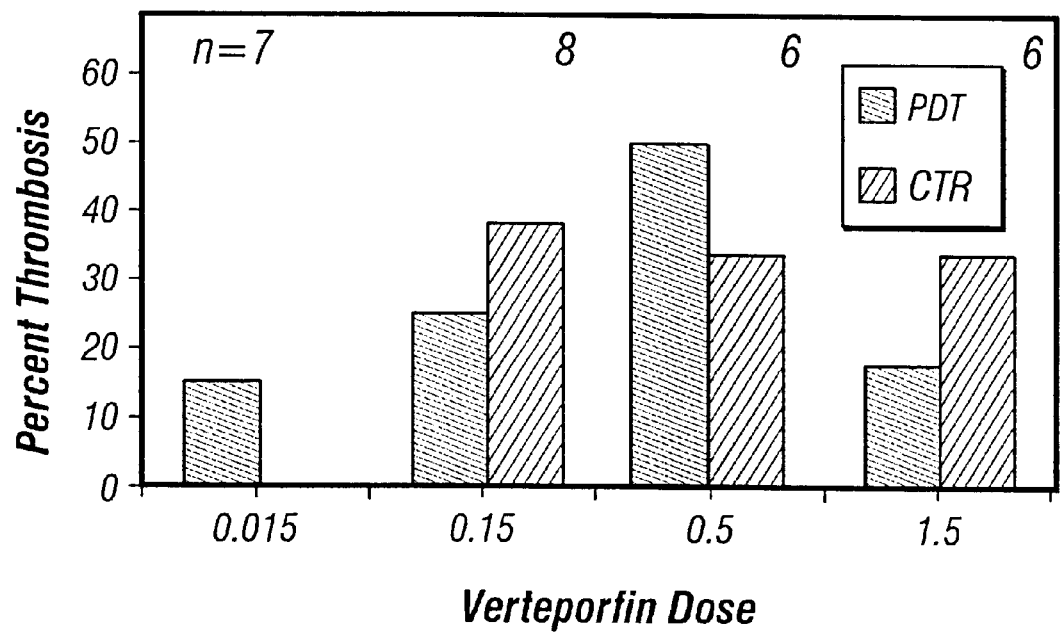
FIG. 5 shows the percent of fistulae which were thrombosed one month after the surgical procedure.

The number of fistulae that thrombosed correlated roughly with increasing drug dose (FIG. 5). However, the average one-month thrombosis incidence for all doses was 26.6% for PDT-treated fistulae and 26.0% for control fistulae.

Figure 6:
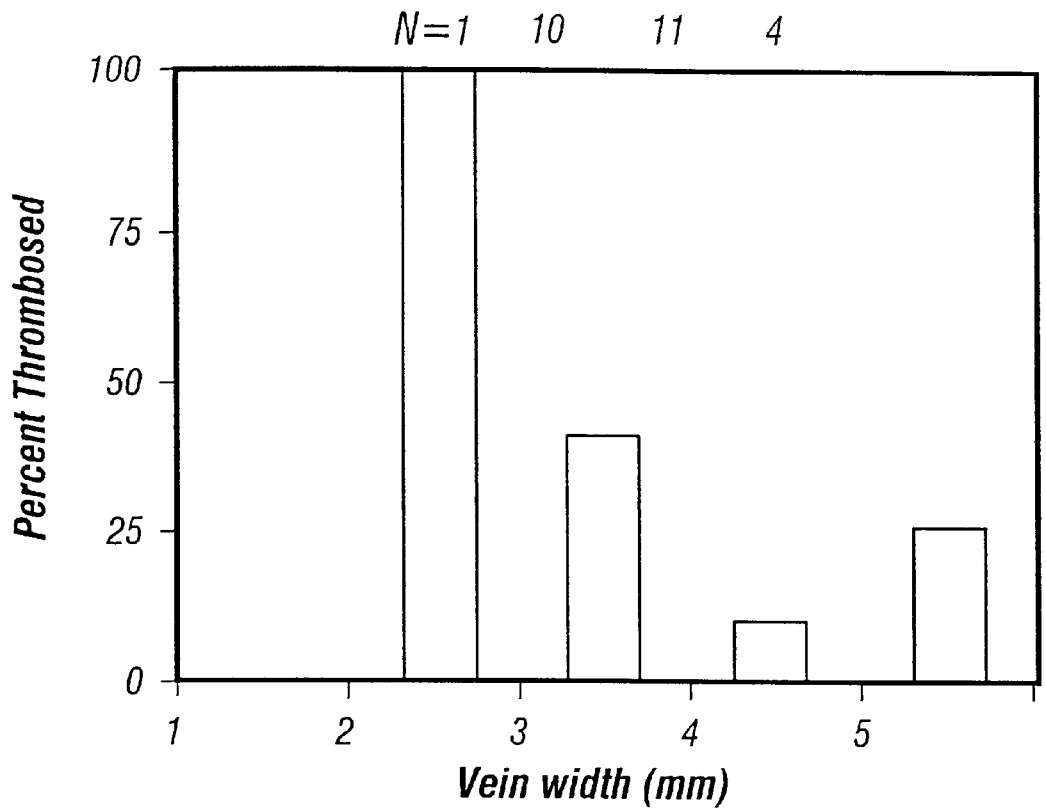
FIG. 6 shows the Percent of control AV-Fistulae thrombosed as a function of vein diameter.

An analysis of the vein size measured upon creating the fistulae revealed that there were other factors influencing the incidence of thrombosis. Looking at control veins only, the percentage of thrombosed fistulae declined as the diameter of the vein increased (FIG. 6). The same trend was observed if PDT-treated vessels were included. Similarly 8/11 pigs with thrombosis were under 50 kg, whereas the remaining 3/11 occurred in pigs between 51 and 80 kg.

Although marked with some doses (0.15 mg), the differences in intimal thickening between PDT-treated and control veins were not statistically significant at one month. Some high variability was observed between pigs.

The severity of IH observed in treated and control vessels may have been muted by the use of heparin as an anticoagulant during the surgical procedures used as part of the invention. Heparin is known to have antiproliferative effects on SMCs and reduce IH (24). Relatively low doses of heparin were necessary however to inhibit thrombosis.

In contrast to intimal thickening, PDT did not affect medial thickening. Medial thickening is a necessary part of fistula maturation. Arterialization of the vein must take place for the fistula to be a successful access site for dialysis needles. However, intimal thickening on top of medial thickening leads to narrowing of the lumen predisposing the vein to thrombosis.

Additionally, low-dose PDT was not associated with an increase in the incidence of thrombosis. However, PDT with high doses of BPD-MA appeared to render the vessel wall more thrombogenic. The averaged incidence of thrombosis observed one month after fistulae creation was comparable to that reported in the literature describing the clinical experience. The failure rate within the first 30 days of AV fistula creation is reported to be 13 to 28 percent (6). These early failures were usually a result of thrombosis. Similar to our results, Tellis et al. reported that, in humans, a vessel diameter of 4 mm or less was associated with a higher failure rate (25).

EXAMPLE 3

Three Month Efficacy Study

A three month study was conducted with bilateral end-to side AV fistulae between the carotid artery and the jugular vein created in 11 pigs. One fistula was treated with 0.15 mg/2 mL BPD-MA and 1 J/cm$^2$ OR lamp light delivered over 40 min; the control fistula received 5% Dextrose and light. Animals were sacrificed 3 months after PDT. The fistulae were surgically excised and processed for histology and morphometric analysis as described previously. Only 27% of the PDT treated and 45% of the control fistulae were patent by 3 months. Occlusion appeared to be due to both early thrombosis, possibly related to the surgical procedure or late thrombosis due to extensive IH and lumen narrowing.

Figure 7:
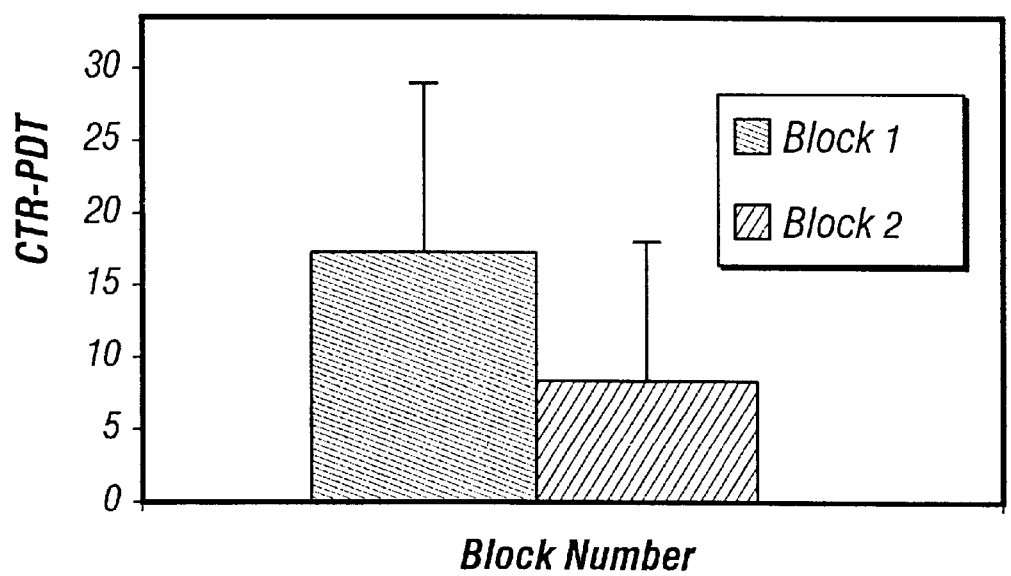
FIG. 7 shows the difference in the percent of the lumen area of the vein compromised by IH between control and PDT-treated fistulae after 3 months (n=3).

There were three animals for which patent PDT-treated and control fistulae could be recovered. The percent of the lumen compromised by IH (% LCIH=EL−Lumen/IEL) was calculated for the first two complete blocks from the tip of the anastamosis for these samples. Differences in the % LCIH between control and PDT-treated fistulae were averaged and presented in FIG. 7.

Figure 8:
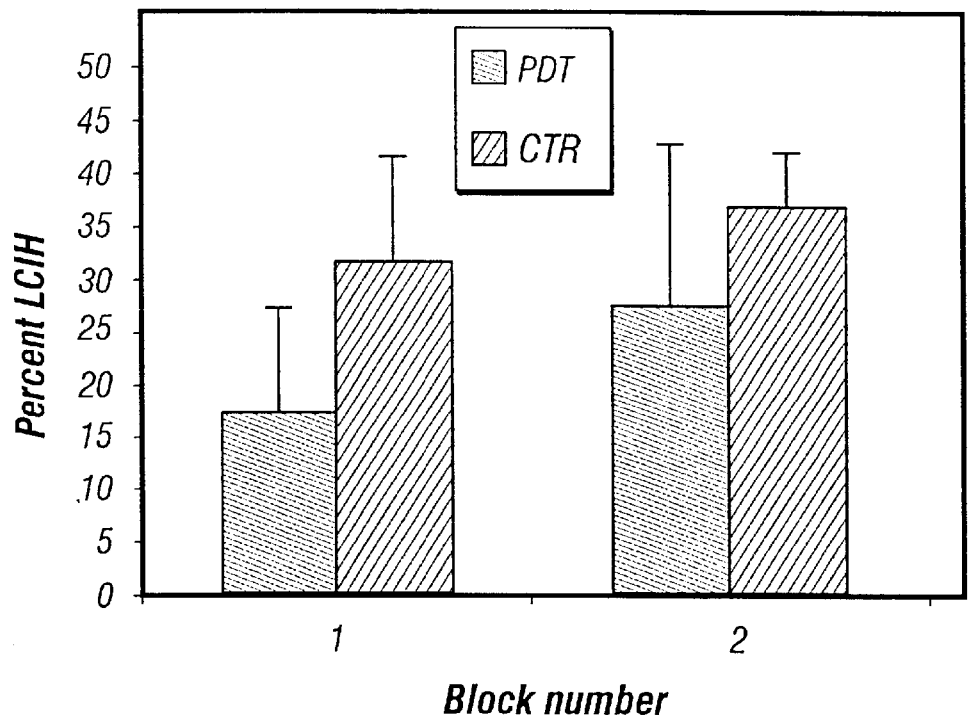
FIG. 8 shows the mean percent IH compromising the lumen in PDT-treated (0.15 mg/2 mL) blocks compared to control blocks after 3 months (n=3).

The average % LCIH in the control group was 31.2% and 36.9% for the first and second blocks respectively (Tables 2a and 2b). The PDT-induced decrease in intimal hyperplasia translated into a relative reduction of 46% for block 1, and a 27% relative reduction for block 2 (FIG. 8).

TABLE 2A

Percent Lumen Compromised by Intimal Hyperplasia (Three Month Data)
0.15 mg VERTEPORFIN
Percent Lumen Compromised by Intimal Hyperplasia

| | PDT | | Control | | Control-PDT | |
|---|---|---|---|---|---|---|
| Pig # | | Block#2 | Block#1 | Block#2 | Block#1 | Block#2 |
| 1 | 17.3 | 46.4 | 49.1 | 39.8 | 31.8 | −6.6 |
| 2 | 3.1 | 2 | 2.7 | 19.6 | −0.4 | 17.6 |
| 3 | 30.2 | 32.3 | 49.0 | 46.8 | 18.8 | 14.5 |
| 4 | T | 41.7 | 41.7 | 40.2 | | |
| 5 | T | 13.7 | 13.7 | 38.3 | | |
| Mean | 16.9 | 26.9 | 31.2 | 36.9 | 16.7 | 8.5 |
| STD | 13.6 | 22.7 | 21.6 | 10.2 | 16.2 | 13.2 |
| SEM | 9.6 | 16.0 | 10.8 | 5.1 | 11.5 | 9.3 |

TABLE 2B

Medial Hyperplasia (Three month Data)
0.15 mg VERTEPORFIN
Medial Hyperplasia

| | PDT | | Control | |
|---|---|---|---|---|
| Pig # | Block#1 | Block#2 | Block#1 | Block#2 |
| 1 | 38.1 | 27.5 | 36.8 | 32.4 |
| 2 | 17.3 | 9.2 | 26.1 | 7.8 |
| 3 | 8.4 | 8.1 | 15.9 | 15.9 |
| 4 | | | 28.0 | 16.7 |
| 5 | | | 12.6 | 31.6 |
| Mean | 21.3 | 14.9 | 23.9 | 20.9 |
| STD | 15.2 | 10.9 | 9.7 | 10.7 |
| SEM | 10.8 | 7.7 | 4.9 | 5.4 |

The rate of occlusion in the swine kept for 3 months after fistula creation was unacceptably high. This may be a limitation of the swine model reflected in the fact that published studies rarely include data from beyond the one month time-point (21). However, analysis of the three animals that maintained both fistulae patent revealed a marked decrease in IH in the block of tissue immediately adjacent to the anastamosis. IH in the vein is most often observed clinically within one centimeter of the anastamosis. This is apparently the first report that PDT successfully inhibited IH at the vein anastomosis. Other PDT protocols have successfully suppressed IH only in the body of vein grafts without affecting IH at the anastamosis (21).

Figure 9:
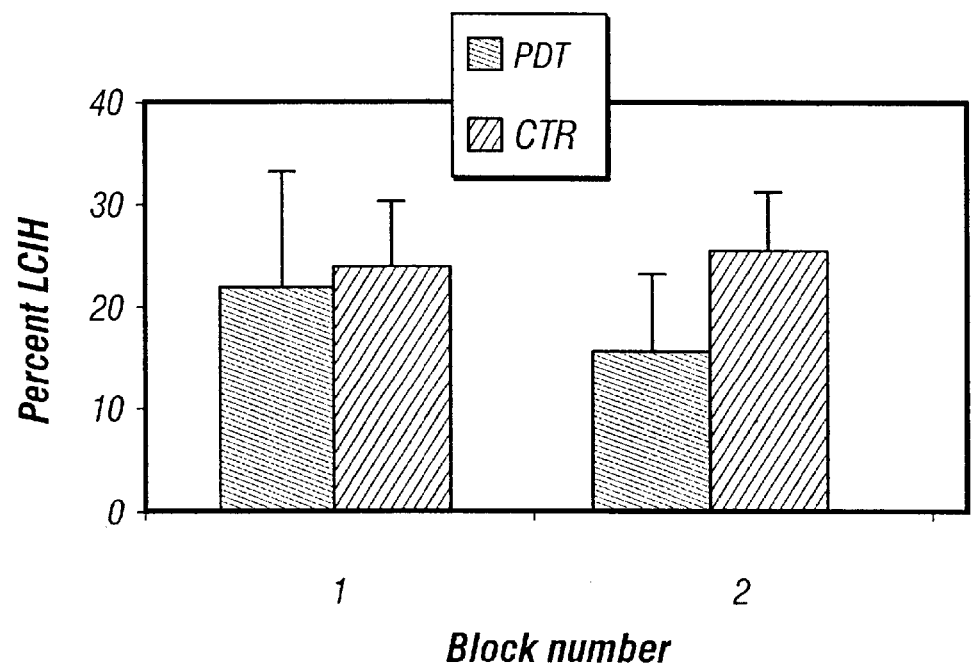
FIG. 9 shows the mean percent medial hyperplasia in PDT-treated blocks and control blocks after 3 months (n=3).

After 3 months little PDT effect was observed on the media of the veins (FIG. 9). Although PDT may reduce IH, it does not affect the longer term arterialization of the vein suggesting that PDT-treated veins would mature satisfactorily to be used for vascular access.

EXAMPLE 4

Cellular Effects of PDT on AV Fistulae

For the purposes of determining the early cellular effects of PDT on the vein, bilateral AV fistulae were created in six pigs and treated sides were given 0.15 mg BPD-MA (0.15 mg/2 mL) and 40 minutes OR light. After 48 hours these pigs were sacrificed and the fistulae were recovered and processed for histological evaluation. This is not enough time for IH to have developed, but the cellular activation which leads to IH may be detectable. No significant difference in the area of the veins that stained positively for SMC was observed between PDT-treated and control veins, which may be expected at this early time-point. Immunocytochemistry for the proliferating cell nuclear antigen (PCNA) was used to assess cell proliferation in the tissue (Table 3).

Low-dose PDT reduced by 2-fold the number of proliferating cells that appear at the anastomosis of the vein following grafting. It is tempting to conclude that PDT has inhibited SMC proliferation, but other PCNA positive cells in the vein wall may have also included infiltrating macrophages or T cells as well as myofibroblasts (23).

TABLE 3

MEAN PERCENT OF PCNA POSITIVE CELLS PER TISSUE AREA

|  | CTR | | PDT | |
|---|---|---|---|---|
|  | Mean | SEM | Mean | SEM |
| BLOCK 1 | 0.61 | 0.28 | 0.33 | 0.07 |
| BLOCK 2 | 0.68 | 0.21 | 0.74 | 0.12 |
| BLOCK 3 | 0.74 | 0.15 | 0.65 | 0.10 |

The data suggest that PDT reduced the number of proliferating cells in block 1, the section of the vein immediately adjacent to the anastomosis. The PCNA staining was visible in the media of both PDT-treated and control veins (FIGS. 10a–10d).

An increase in PCNA-positive SMCs in the control veins would be expected to lead to a greater number or area of the vessels being occupied by SMC by the one-month time-point. This greater number of SMCs and the extraceilular matrix that activated, synthetic SMCs produce may have resulted in the increased IH observed in the first two blocks of the one-and three-month control pigs compared to those treated with 0.15 mg BPD-MA.

Figure 10:
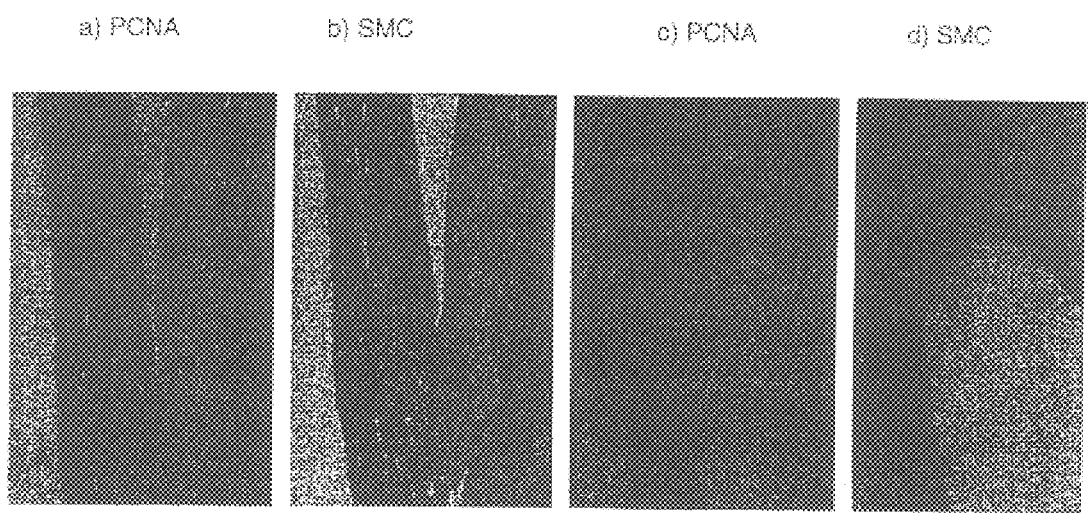
FIGS. 10a–10d show immunohistochemical staining for PCNA and alpha-smooth muscle actin (10× magnification). Representative venous portions of sections taken from AV fistulae excised 48 hours after treatment are shown. PDT treated vein samples were stained for PCNA (10a) and SMCs (10b). Saline treated (control) vein samples were stained for PCNA (10c) and SMCs (10d).

Immunocytochemical staining for x-smooth muscle actin was used to identify SMC (FIGS. 10b and 10d). Quantitation of the percentage of the total tissue area which was stained positively for SMC revealed minor differences between PDT-treated and control fistulae 48 hours after fistulae creation (Table 4).

TABLE 4

Mean Percent of the Total Tissue Area Which was α-actin Positive

|  | CTR | | PDT | |
|---|---|---|---|---|
|  | Mean | SEM | Mean | SEM |
| BLOCK 1 | 1.79 | 0.69 | 1.94 | 0.68 |
| BLOCK 2 | 2.76 | 0.71 | 3.06 | 0.60 |
| BLOCK 3 | 1.89 | 0.51 | 2.81 | 0.28 |

Staining macrophages and T cells provide an indication of the possible immune responses occurring in the vein wall following PDT. Cells stained positively by the anti-monocyte/macrophage antibody were counted in the intima/media and adventitia of the vein cross-sections separately. In all cases at least twice as many macrophages were counted in the adventitia than the intima/media layers of the veins (FIGS. 11a and 11b). CD3 positive T cells we re observed in the adventitia but were scarce. At 48 hours low-dose PDT did not affect the number of leukocytes infiltrating the veins as compared to control veins.

Figure 12:
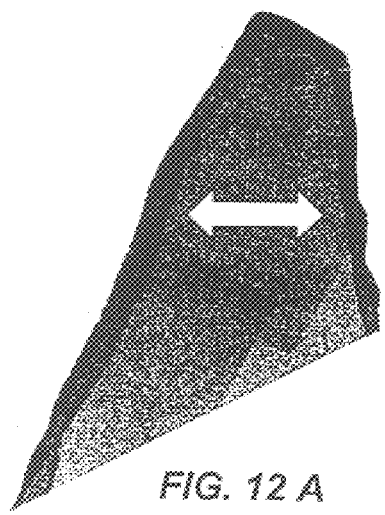
FIGS. 12A–12C show immunohistochemical staining for endothelial cells.
Figure 12:
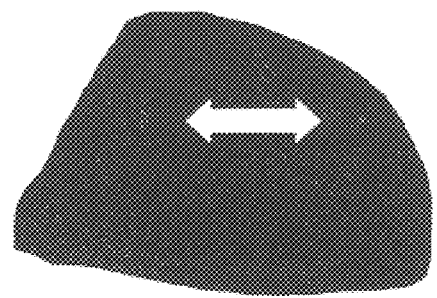

Immunocytochemical staining for von Willebrand factor was performed to characterize the effects of PDT on the endothelial lining of the vein lumen. Low-dose PDT did not appear to damage the endothelial cell lining of the treated veins (FIGS. 12A and 12B). This was reflected by the rate of thrombosis in the one month PDT-treated pigs which was similar to the average level of control veins.

Figure 12C:
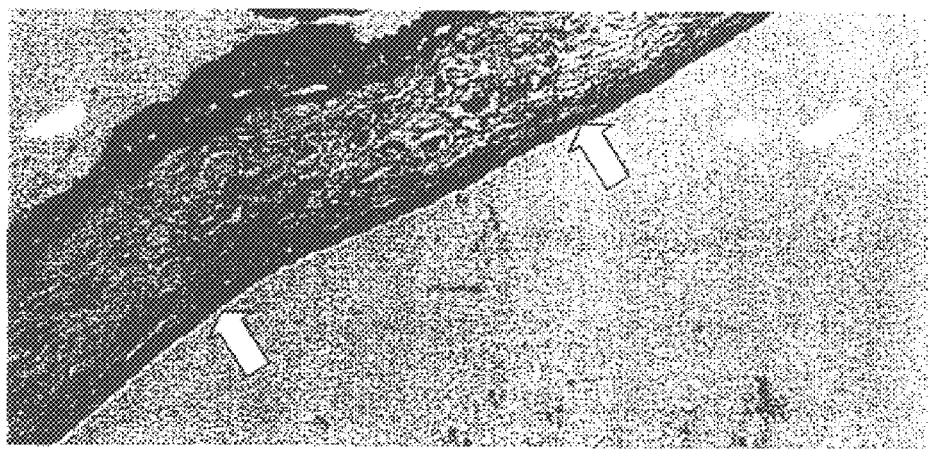

Elastin (Verhoeff's elastic) staining performed on 48 h and 1 month samples showed no sign of damage to the elastic lamina due to PDT (FIG. 12C).

All references cited herein are hereby incorporated by reference in their entireties, whether previously specifically incorporated or not. As used herein, the terms "a", "an", and "any" are each intended to include both the singular and plural forms.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

REFERENCES

1. Luke, R. G. (1998). Chronic renal failure-a vasculopathic state. *N Engl J Med*, 339, 841–3.

2. Byrne, C., Vernon, P. & Cohen, J. J. (1994). Effect of age and diagnosis on survival of older patients beginning chronic dialysis. *Jama*, 271, 34–6.

3. Hurt, A. V., Batello-Cruz, M., Skipper, B. J., Teaf, S. R. & Sterling, W. A., Jr. (1983). Bovine carotid artery heterografts versus polytetrafluoroethylene grafts. A prospective, randomized study. *Am J Surg*, 146, 844–7.

4. Tellis, V. A., Kohlberg, W. I., Bhat, D. J., Driscoll, B. & Veith, F. J. (1979). Expanded polytetrafluoroethylene graft fistula for chronic hemodialysis. *Ann Surg*, 189, 101–5.

5. Burbridge, G. E., Biggers, J. A., Remmers, A. R., Jr., Lindley, J. D., Saries, H. E. & Fish, J. C. (1976). Late complications and results of bovine xenografts. *Trans Am Soc Artif Intern Organs*, 22, 377–81.

6. Leapman, S. B., Boyle, M., Pescovitz, M. D., Milgrom, M. L., Jindal, R. M. & Filo, R. S. (1996). The arteriovenous fistula for hemodialysis access: gold standard or archaic relic? *Am Surg*, 62, 652–6; discussion 656–7.

7. Leapman S B, P. M.; Thomalla J V, Milgrom M and Filo R S. (1993). *Vascular Access for Hemodialysis-III*. W L Gore and Associates, Inc. and Precept Press.

8. Humphries A L, H. W., Wynn J J, nesbit R R, Caruana R J, Wray C H. (1989). *Alternative plans for vascular access for hemodialysis*. Vol. I. Vascular Access for Hemodialysis. W L Gore and Associates, Inc. and Pluribus Press, Inc.

9. Dilley, R. J., McGeachie, J. K. & Prendergast, F. J. (1988). A review of the histologic changes in vein-to-artery grafts, with particular reference to intimal hyperplasia. *Arch Surg*, 123, 691–6.

10. Kaplan M P, T. M. (1989). *An analysis of early (two week) failure of vascular access*. Vol. III. Vascular Access for Hemodialysis. W L Gore and Associates, Inc. and Pluribus Press, Inc.

11. Excerpts from the United States Renal Data System Annual Report (1998) *American J. Kidney Dis.*, 32, S9-S141.

12. Diskin C J, S. T., Pennell A T. (1993). *Pharmacological intervention to prevent intimal hyperplasia.* Vol. III. Vascular Access For Hemodialysis. W L Gore and Associates, Inc. and Precept Press, Inc.

13. Dougherty, T. J. (1987). Photosensitizers: therapy and detection of malignant tumors. *Photochem Photobiol*, 45, 879–89.

14. Statius van Eps, R. G., Adili, F., Watkins, M. T., Anderson, R. R. & LaMuraglia, G. M. (1997). Photodynamic therapy of extracellular matrix stimulates endothelial cell growth by inactivation of matrix-associated transforming growth factor-beta. *Lab Invest*, 76, 257–66.

15. Hunt, D. W., Jiang, H., Granville, D. J., Chan, A. H., Leong, S. & Levy, J. G; (1999). Consequences of the photodynamic treatment of resting and activated peripheral T lymphocytes. *Immunopharmacology*, 41, 31–44.

16. Hunt, D. W. C. & Chan, A. H. (1999). Photodynamic therapy and immunity. *IDrugs.* 2, 231–236.

17. LaMuraglia, G. M., ChandraSekar, N. R., Flotte, T. J., Abbott, W. M., Michaud, N. & Hasan, T. (1994). Photodynamic therapy inhibition of experimental intimal hyperplasia: acute and chronic effects. *J Vasc Surg*, 19, 321–9; discussion 329–31.

18. Ortu, P., LaMuraglia, G. M., Roberts, W. G., Flotte, T. J. & Hasan, T. (1992). Photodynamic therapy of arteries. A novel approach for treatment of experimental intimal hyperplasia. *Circulation*, 85, 1189–96.

19. Dartsch, P. C., Ischinger, T. & Betz, E. (1990). Responses of cultured smooth muscle cells from human nonatherosclerotic arteries and primary stenosing lesions after photoradiation: implications for photodynamic therapy of vascular stenoses. *J Am Coll Cardiol*, 15,1545–50.

20. Sobeh, M. S., Chan, P., Ham, R. J., Wood, A. J. & Cross, F. W. (1995). Photodynamic therapy in a cell culture model of human intimal hyperplasia. *Eur J Vasc Endovasc Surg*, 9, 463–8.

21. LaMuraglia, G. M., Klyachkin, M. L., Adili, F. & Abbott, W. M. (1995). Photodynamic therapy of vein grafts: suppression of intimal hyperplasia of the vein graft but not the anastomosis. *J Vasc Surg*, 21, 882–90; discussion 889–90.

22. Pond, W. *Nutrition and the cardiovascular system of swine.* Vol. II. Swine in Cardiovascular Research. CRC Press: Boca Raton Fla.

23. Westerband, A., Mills, J. L., Hunter, G. C., Gentile, A. T., Ihnat, D. & Heimark, R. L. (1998). Topography of cell replication in human vein graft stenoses. *Circulation*, 98, II325–9; discussion II329–30.

24. Sindermann, J. R. & March, K. L. (1998). Heparin responsiveness in vitro as a prognostic tool for vascular graft stenosis: a tale of two cell types? *Circulation*, 97, 2486–90.

25. Tellis, V., Veith, F. J., Attai-Lari, A., Soberman, R. & Gliedman, M. L. (1969). Internal arteriovenous fistulae in a hemodialysis-transplant program. *Trans Am Soc Artif Intern Organs*, 15, 293–7

What is claimed is:

1. A method to prevent, treat, inhibit, or reduce intimal hyperplasia in a vein graft, artery graft or vascular graft in a subject, which method comprises contacting said graft in vivo with a photosensitizer at a concentration and for a time effective to photosensitive said graft tissue, and irradiating said photosensitized graft with radiation at a wavelength absorbed by the photosensitizer for a time and at an intensity to prevent, treat, inhibit, or reduce intimal hyperplasia in said graft, wherein the concentration, of the photosensitizer, the intensity of the radiation, and the total energy provided are adjusted to provide said graft with low-dose photodynamic therapy, and said graft optionally comprises a prosthetic conduit.

2. The method of claim 1 wherein the graft is a vein graft.

3. The method of claim 1 wherein said irradiating and contacting-steps are performed simultaneously.

4. The method of claim 1 wherein said irradiating step is conducted subsequent to the contacting step.

5. The method of claim 1 wherein said graft is an arteriovenous fistula.

6. The method of claim 1 wherein said prevention, treatment, inhibition, or reduction in intimal hyperplasia occurs at the anastomosis of the graft.

7. The method of claim 1 wherein the photosensitizer is a porphyrin derivative.

8. The method of claim 7 wherein the porphyrin derivative is porfimer sodium or a green porphyrin.

9. The method of claim 8 wherein the green porphyrin is BPD-MA or A-EA6.

10. The method of claim 1 wherein said subject is human.

11. The method of claim 10 wherein said human is undergoing kidney dialysis.

12. The method of claim 2 wherein said irradiating and contacting steps are performed simultaneously.

13. The method of claim 2 wherein said irradiating step is conducted subsequent to the contacting step.

14. The method of claim 2 wherein said graft is an arteriovenous fistula.

15. The method of claim 2 wherein said prevention, treatment, inhibition, or reduction in intimal hyperplasia occurs at the anastomosis of the graft.

16. The method of claim 2 wherein the photosensitizer is a porphyrin derivative.

17. The method of claim 16 wherein the porphyrin derivative is porfimer sodium or a green porphyrin.

18. The method of claim 17 wherein the green porphyrin is BPD-MA or A-EA6.

19. The method of claim 2 wherein said subject is human.

20. The method of claim 19 wherein said human is undergoing kidney dialysis.

21. The method of claim 1 wherein said graft comprises a prosthetic conduit.

22. A method to prevent, treat, inhibit, or reduce intimal hyperplasia in an arteriovenous (AV) fistula in a subject, which method comprises contacting said AV fistula with a photosensitizer at a concentration and for a time effective to photosensitive said AV fistula tissue, and irradiating said photosensitized AV fistula with radiation at a wavelength absorbed by the photosensitizer for a time and at an intensity to prevent, treat, inhibit, or reduce intimal hyperplasia in said AV fistula, wherein the concentration of the photosensitizer, the intensity of the radiation, and the total energy provided are adjusted to provide said AV fistula with low-dose photodynamic therapy and wherein said prevention, treatment, inhibition, or reduction in intimal hyperplasia occurs at the anastomosis of the AV fistula.

\* \* \* \* \*